United States Patent [19]

Inaba et al.

[11] Patent Number: 5,151,431
[45] Date of Patent: Sep. 29, 1992

[54] 4,5-DIHYDRO-6H-IMIDAZO[4,5,1-IJ]QUINO-LIN-6-ONE-6-OXIME-O-SULFONIC ACID DERIVATIVES USEFUL FOR TREATING HYPERTENSION OR EDEMA

[75] Inventors: Hitoshi Inaba; Kazumi Nishijima; Kazuo Kato; Ichiro Yamamoto; Ei Mochida, all of Shinjuku; Kikuo Ohtomo, Kita, all of Japan

[73] Assignees: Mochida Pharmaceutical Co., Ltd.; Hodogaya Chemical Co., Ltd., both of Tokyo, Japan

[21] Appl. No.: 540,950

[22] Filed: Jun. 20, 1990

[30] Foreign Application Priority Data

Jun. 26, 1989 [JP] Japan .................................. 1-163190

[51] Int. Cl.$^5$ .................... C07D 471/04; A61K 31/44
[52] U.S. Cl. ........................................ 514/292; 546/87
[58] Field of Search ........................... 546/87; 514/292

[56] References Cited

U.S. PATENT DOCUMENTS 3,200,123  8/1965  Richardson, Jr. et al. ............ 546/84
4,609,655  9/1986  Crossley ............................... 514/292
4,703,044  10/1987  Crossley ............................... 514/214

OTHER PUBLICATIONS

Chemical Abstracts, vol. 79, No. 21, Nov. 26, 1973, Columbus, Ohio I. G. Il'Ina et al., "Synthesis of Some Thionoimidazole Structures of Quinoline and Indole Series", p. 400, col. 2.

*Primary Examiner*—Alan L. Rotman
*Attorney, Agent, or Firm*—Oliff & Berridge

[57] ABSTRACT

The present invention relates to novel 4,5-dihydro-6H-imidazo[4,5,1-ij]quinolin-6-one-6-oxime-O-sulfonic acid compounds, processes for producing said compounds, intermediate compounds, i.e. novel 4,5-dihydro-6H-imidazo[4,5,1-ij]quinolin-6-one compounds and 4,5-dihydro-6H-imidazo[4,5,1-ij]quinolin-6-one-6-oxime compounds in the synthesis of said compounds, processes for producing said intermediate compounds, and pharmaceutical or veterinary compositions containing said compounds.

The present invention is based on the selection of the substituents of 4,5-dihydro-6H-imidazo[4,5,1-ij]-quinolin-6-one-6-oxime-O-sulfonic acid compounds at 2-position, namely 2-(2-penten-3-yl)-, 2-cyclohexyl-, 2-naphthyl-, 2-thienyl-, etc.

The compounds of the present invention containing these substituents have potent hypotensive, anti-oedematous and diuretic effects as well as an activity of removing ascites. The compounds of the present invention are extremely useful for treatment of diseases and disorders mentioned above.

30 Claims, No Drawings

4,5-DIHYDRO-6H-IMIDAZO[4,5,1-IJ]QUINOLIN-6-ONE-6-OXIME-O-SULFONIC ACID DERIVATIVES USEFUL FOR TREATING HYPERTENSION OR EDEMA

BACKGROUND OF THE INVENTION

The present invention relates to novel 4,5-dihydro-6H-imidazo[4,5,1-ij]quinolin-6-one-6-oxime-O-sulfonic acid compounds, processes for producing said compounds, intermediate compounds, i.e. novel 4,5-dihydro-6H-imidazo[4,5,1-ij]quinolin-6-one compounds and 4,5-dihydro-6H-imidazo[4,5,1-ij]quinolin-6-one-6-oxime compounds in the synthesis of said compounds, processes for producing said intermediate compounds, and compositions containing said compounds with potent diuretic activity that can be used for the treatment and/or the prevention of hypertension, oedema and/or for the removal of ascites.

For the treatment of hypertension, benzothiazide derivatives such as trichloromethiazide or so-called loop diuretics such as furosemide have widely been used to lower blood pressure. Many of these diuretics, however, are known to show several adverse reactions in common, for example, unbalances of electrolytes such as hypokalemia; hyperuricemia; digestive troubles such as nausea or vomiting; blood troubles such as thrombocytopenia or leukopenia; decrease in glucose tolerance; and disorders in lipid metabolism. Even in furosemide, several adverse reactions such as hypokalemia, hyperuricemia or disorders in sugar metabolism have frequently been reported.

Diuretics have also been used for the treatment of oedema resulted from retention of water and electrolytes based on cardiac, renal or hepatic insufficiencies or on metabolic disorders, but in the case of the treatment of ascites which is often observed in the patients with abdominal tumor or liver cirrhosis, these conventionally used diuretics show only marginal effect to the removal of ascites.

These benzothiazide diuretics and loop diuretics are known to have similar chemical structures.

With the foregoing background, it has been desired to develop novel diuretics that have potent diuretic activities and are useful for the treatment of hypertension, oedema and ascites and that do not cause aforementioned adverse reactions by synthesizing compounds whose chemical structures are novel and different from those of known diuretics.

SUMMARY OF THE INVENTION

An object of the present invention is to provide novel 4,5-dihydro-6H-imidazo[4,5,1-ij]quinolin-6-one-6-oxime-O-sulfonic acid compounds, or salts or solvates or solvates of said salts thereof.

Another object of the present invention is to provide processes for producing novel 4,5-dihydro-6H-imidazo[4,5,1-ij]quinolin-6-one-6-oxime-O-sulfonic acid compounds.

A further object of the present invention is to provide compositions for the treatment of hypertension, oedema and ascites which comprise novel 4,5-dihydro-6H-imidazo[4,5,1-ij]quinolin-6-one-6-oxime-O-sulfonic acid compounds as active components.

A further object of the present invention is to provide intermediate compounds, novel 4,5-dihydro-6H-imidazo[4,5,1-ij]quinolin-6-one compounds and 4,5-dihydro-6H-imidazo[4,5,1-ij]quinolin-6-one-6-oxime compounds, in the synthesis of 4,5-dihydro-6H-imidazo[4,5,1-ij]quinolin-6-one-6-oxime-O-sulfonic acid compounds and to provide processes for producing such intermediate compounds.

The present invention is based on the selection of the substituents of 4,5-dihydro-6H-imidazo[4,5,1-ij]quinolin-6-one-6-oxime-O-sulfonic acid compounds at 2-position, namely 2-(2-penten-3-yl)-, 2-cyclohexyl-, 2-naphthyl-, 2-thienyl-, etc.

The compounds of the present invention containing these substituents have potent hypotensive, antioedematous and diuretic effect as well as an activity to remove ascites and are extremely useful for the treatment of diseases and disorders mentioned above.

DETAILED DESCRIPTION OF THE INVENTION

As a result of extensive investigations concerning development of novel dihydroimidazoquinolinone oxime sulfonic acid compounds having a satisfactory diuretic activity, the present inventors have found that 4,5-dihydro-6H-imidazo[4,5,1-ij]quinolin-6-one-6-oxime-O-sulfonic acid compounds possess potent diuretic activities and are useful for the treatment and/or the prevention of hypertension, oedema and/or for the removal of ascites, thus satisfy these requirements, and have accomplished the present invention.

The present invention is directed to 4,5-dihydro-6H-imidazo[4,5,1-ij]quinolin-6-one-6-oxime-O-sulfonic acid compounds represented by the formula (I):

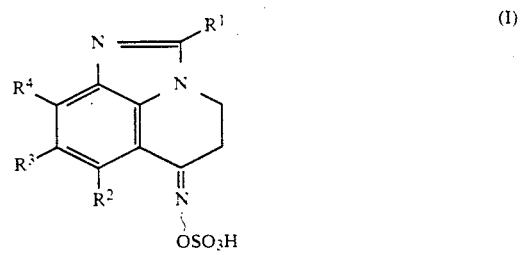

wherein $R^1$ represents

wherein A represents an alkylene of straight or branched chain having 1 to 10 carbon atoms, an alkenylene of straight or branched chain having 2 to 10 carbon atoms, B represents a hydrogen atom, a hydroxy group, an optionally substituted cycloalkyl or cycloalkenyl group having 3 to 8 carbon atoms, an optionally substituted phenyl group, an optionally substituted phenoxy group, an optionally substituted naphthyl group or an optionally substituted mono- or fused-heterocyclic group, m represents 0 or an integer of 1 and $R^2$, $R^3$ and $R^4$ are identical or different and represent hydrogen atoms, halogen atoms, hydroxy groups, alkyl groups having 1 to 4 carbon atoms, alkoxy groups having 1 to 4 carbon atoms or halogenated alkyl groups having 1 to 4 carbon atoms, and the bond shown with a wavy line represents a bond of E-form or Z-form, or a salt or a solvate or a solvate of said salt thereof.

The present invention is also directed to processes for preparing above-mentioned 4,5-dihydro-6H-imidazo[4,5,1-ij]quinolin-6-one-6-oxime-O-sulfonic acid compounds.

The present invention is further directed to pharmaceutical compositions with potent diuretic activities useful for the treatment and/or the prevention of hypertension, oedema and/or for the removal of ascites, uric acids and/or for the regulation of balances of electrolytes characterized by containing these 4,5-dihydro-6H-imidazo[4,5,1-ij]quinolin-6-one-6-oxime-O-sulfonic acid compounds as active components. In addition to above-mentioned pharmaceutical effects, these compounds are metabolically stable, little toxic and presumed safety at pharmaceutically effective doses. So, these compounds are useful for the treatment and/or the prevention of hypertensions such as essential hypertension, renal hypertension or pernicious hypertension etc., and/or oedemas such as congestive heart failure, renal oedema, hepatic oedema, gestosis, pregnant oedema or oedema by disturbances of peripheral circulation etc., and/or ascites such as ascites seen in patient with abdominal tumor or liver cirrhosis.

The present invention is also directed to intermediate compounds, novel 4,5-dihydro-6H-imidazo-[4,5,1-ij]quinolin-6-one compounds and 4,5-dihydro-6H-imidazo[4,5,1-ij]quinolin-6-one-6-oxime compounds, in the synthesis of 4,5-dihydro-6H-imidazo[4,5,1-ij]quinolin-6-one-6-oxime-O-sulfonic acid compounds and processes for producing such intermediate compounds.

The compounds of the present invention represented by the formula (I) are chemically novel and can generally be produced according to the following reaction scheme:

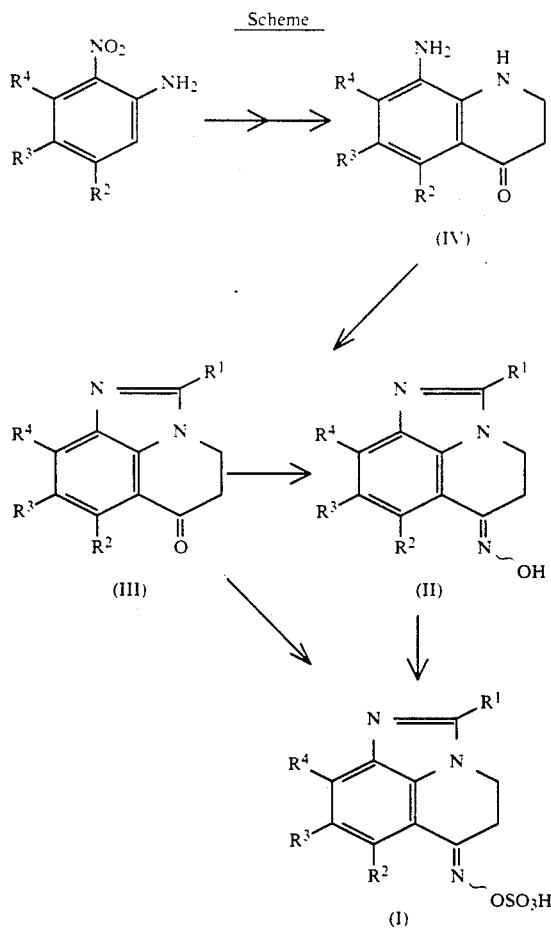

Details of the processes are described below.

PREPARATION OF A COMPOUND REPRESENTED BY THE FORMULA (IV)

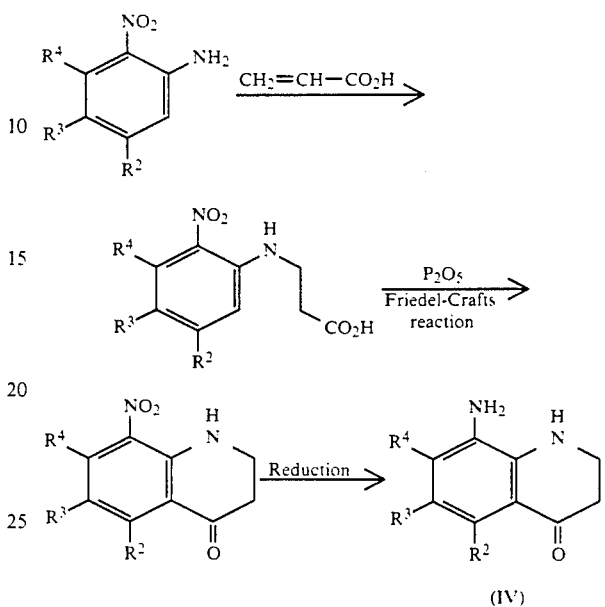

By Friedel-Crafts reaction, known compounds 3-(2nitrophenylamino)propionic acid, 3-(4-chloro-2-nitrophenylamino)propionic acid, 3-(3-chloro-2-nitrophenylamino)propionic acid [Ann. Chim. (Rome), volume 55, page 182 (1965)] or substituted N-(2-carboxyethyl)-2-nitroanilin compounds, which can generally be prepared by reacting known substituted 2-nitroaniline with acrylic acid, are converted into novel 2,3-dihydro-8-nitro-4(1H)-quinolinone compounds such as 7-chloro-2,3-dihydro-8-nitro-4(1H)-quinolinone, 6-fluoro-2,3-dihydro-8-nitro-4(1H)-quinolinone and 2,3-dihydro-7-methyl-8-nitro-4(1H)-quinolinone. The 2,3-dihydro-8-nitro-4(1H)-quinolinone compounds are reduced by tin chloride - hydrochloric acid, tin - hydrochloric acid, iron - hydrochloric acid, iron - acetic acid or by catalytic hydrogenation to give 8-amino-2,3-dihydro-4(1H)-quinolinone compounds represented by the formula (IV):

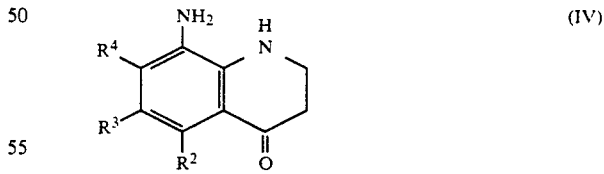

wherein $R^2$, $R^3$ and $R^4$ have the same significances as defined above.

Instead of acrylic acid, acrylic acid ester or acrylonitrile can be used in foregoing reaction. In these cases, following hydrolyses of the products are necessary to obtain carboxylic acid derivatives to be applied to the next reaction.

In the above Friedel-Crafts reaction, sulfuric acid, phosphoric acid, polyphosphoric acid, polyphosphoric acid ester or phosphorus pentoxide, etc., preferably, phosphorus pentoxide can be used.

PREPARATION OF THE COMPOUND REPRESENTED BY THE FORMULA (III)

method A

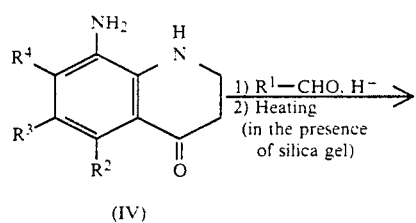

method B

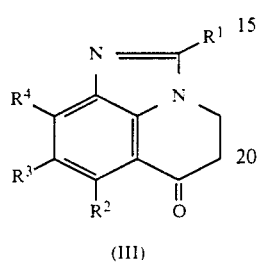

method C

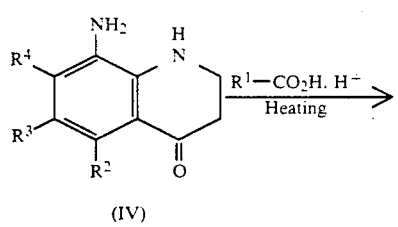

Method A

A compound represented by the formula (IV) and an appropriate aldehyde derivative in lower alcohol (such as methanol, ethanol, etc.) are heated at 20° C. to 40° C. in the presence of a little inorganic acid (such as hydrochloric acid, hydrobromic acid, etc.), then added silica gel and a halogenated hydrocarbon (such as dichloromethane, dichloroethane, etc.). After removing the solvent in vacuo, the residue is heated at 60° C. to 100° C. to give 4,5-dihydro-6H-imidazo[4,5,1-ij]-quinolin-6-one compound, an intermediate compound represented by the formula (III):

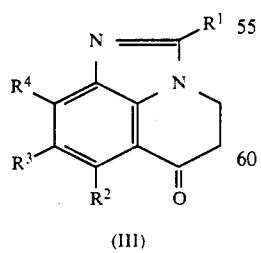

wherein $R^1$, $R^2$, $R^3$ and $R^4$ have the same significances as defined above.

As an aldehyde applied in this reaction, represented by the formula (V):

$$R^1-CHO \qquad (V)$$

wherein $R^1$ has the same significance as defined above, an aliphatic aldehyde (such as nonylaldehyde, 2-ethylbutylaldehyde, 2-ethyl-2-butenal, cyclohexanecarboxyaldehyde, phenylacetoaldehyde, etc.), an aromatic aldehyde (such as benzaldehyde, naphthaldehyde, etc.), an aldehyde having a heterocyclic moiety (such as thiophencarboxyaldehyde, furaldehyde, quinolinecarboxyaldehyde, etc.), etc. can be used.

Method B

A compound represented by the formula (IV) and an appropriate orthoester derivative (such as trimethyl orthoformate, trimethyl orthobenzoate, etc.) in aromatic hydrocarbons (such as benzene, toluene, etc.) are refluxed in the presence of a little p-toluene-sulfonic acid further to give a foregoing intermediate compound represented by the formula (III).

Method C

A compound represented by the formula (IV) and an appropriate aliphatic carboxylic acid derivative (such as 3-hydroxypropionic acid, 4-chlorophenylacetic acid, thienylacetic acid, etc.) or aromatic carboxylic acid derivative (such as benzoic acid, etc.) in 3 to 6M hydrochloric acid are refluxed further to give a foregoing intermediate compound represented by the formula (III).

PREPARATION OF THE COMPOUND REPRESENTED BY THE FORMULA (II)

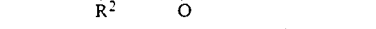

-continued

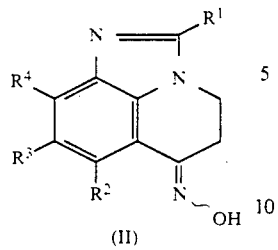
(II)

A compound represented by the formula (III) thus obtained are reacted with an inorganic salt of hydroxylamine in organic solvents (such as methanol, ethanol, tetrahydrofuran, N,N-dimethylformamide, etc.) in the presence of an appropriate base (such as pyridine, N,N-dimethylaniline, potassium acetate, potassium carbonate, sodium carbonate, etc.) to give 4,5-dihydro-6H-imidazo[4,5,1-ij]quinolin-6-one-6-oxime derivative represented by the formula (II):

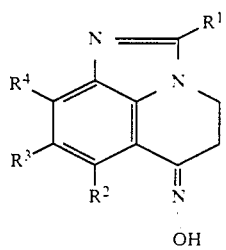
(II)

wherein $R^1$, $R^2$, $R^3$, $R^4$ and the wavy line have the same significances as defined above.

PREPARATION OF THE COMPOUND REPRESENTED BY THE FORMULA (I)

method A

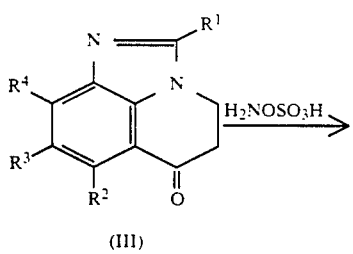

method B

-continued

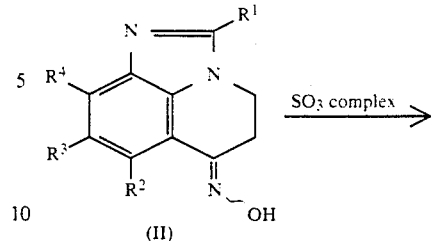
(II)

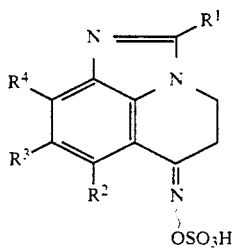
(I)

Method A

A compound represented by the formula (III) are reacted with hydroxylamine-O-sulfonic acid in organic solvents (such as methanol, ethanol, tetrahydrofuran, N,N-dimethylformamide, etc.) to give 4,5-dihydro-6H-imidazo[4,5,1-ij]quinolin-6-one-6-oxime-O-sulfonic acid compound represented by the formula (I):

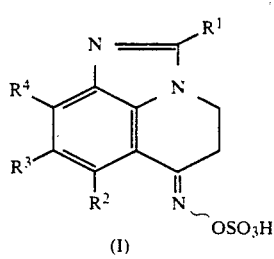
(I)

wherein $R^1$, $R^2$, $R^3$, $R^4$ and the wavy line have the same significances as defined above.

Method B

A compound represented by the formula (II) are also reacted with an sulfonating agents (such as sulfur trioxide-pyridine complex, sulfur trioxide-N,N-dimethylformamide complex, etc.) to give corresponding 4,5-dihydro-6H-imidazo[4,5,1-ij]quinolin-6-one-6-oxime-O-sulfonic acid compound.

Free sulfonic acid moiety of the compound thus obtained can be reacted with an appropriate organic or inorganic base to obtain corresponding salt.

In the compounds of the present invention represented by the formula (I), as regards group —A—, alkylene or alkenylene can be characterized such as methylene, ethylene, propylene, butylene, pentylene, hexylene, decilene, ethenylene, propenylene, etc., preferably methylene, ethylene, propylene, ethenylene, propenylene, etc.; as regards group -B, an optionally substituted cycloalkyl or cycloalkenyl group having 3 to 8 carbon atoms can be characterized such as cyclopropyl, cyclopentyl, cyclohexyl, cyclooctyl, cyclohexenyl, etc., preferably cyclohexyl or cyclohexenyl, etc.; an optionally substituted mono- or fused-heterocyclic can be defined a mono- or fused-heterocyclic having nitrogen atom and/or oxygen atom and/or sulfur atom, such as pyrrolyl, pyrrolinyl, imidazolyl, pyrazolyl, triazolyl, tetrazolyl, oxazolyl, isoxazolyl, oxadiazolyl, thiazolyl, isothiazolyl, thiazolinyl, thiadiazolyl, thiatriazolyl, thienyl, furyl, pyrrolidinyl, imidazolidinyl, thiazolidinyl, pyridyl or its N-oxide, pyrazinyl, pyrimidinyl, pyridazinyl, piperidyl, piperazinyl, morpholinyl, triazinyl, indolyl, isoindolyl, benzimidazolyl, quinolyl, isoquinolyl, quinazolinyl, cinnolinyl, phthalazinyl, quinoxalinyl, indazolyl, benzotriazolyl, benzoxazolyl, benzoxadiazolyl, benzothiazolyl, benzothiadiazolyl, benzisoxazolyl, benzisothiazolyl, benzothienyl, tetrahydrobenzothienyl, benzofuranyl, isobenzofuranyl, chromenyl, chromanyl, coumarinyl, chromonyl, triazolopyridyl, tetrazolopyridyl, purinyl, thiazolopyrimidinyl, triazolopyrimidinyl, thiadiazolopyrimidinyl, thiazolopyridazinyl, naphthyridinyl, xanthenyl, phenoxathiinyl, phenoxazinyl, phenothiazinyl, carbazolyl etc., preferably thienyl, furyl.

Cycloalkyl, cycloalkenyl, phenyl, phenoxy, naphthyl, mono- or fused-heterocyclic can be substituted by one or more substituents such as halogen atoms, lower alkyl, lower alkoxy, nitro, lower alkylamino, etc., preferably halogen atoms, nitro, N,N-diethylamino, etc.

As regards $R^2$, $R^3$ or $R^4$, hydrogen atoms, halogen atoms or alkoxy having 1 to 4 carbon atoms are preferable, further $R^4$ represents a halogen atom is more preferable, and the bond shown with a wavy line (N-O bond of the oximesulfonic acid derivatives) represents E-form or Z-form.

To demonstrate the representative 4,5-dihydro-6H-imidazo[4,5,1-ij]quinolin-6-one-6-oxime-O-sulfonic acid compound and its structure are shown below.

Compounds in the present invention

Compound 1: 9-chloro-4,5-dihydro-2-phenylmethyl-6H-imidazo[4,5,1-ij]quinolin-6-one-6-oxime-O-sulfonic acid potassium salt Compound 2: 9-chloro-4,5-dihydro-2-(3-pentyl)-6H-imidazo[4,5,1-ij]quinolin-6-one-6-oxime-O-sulfonic acid potassium salt Compound 3: 9-chloro-2-(3-cyclohexen-1-yl)-4,5-dihydro-6H-imidazo[4,5,1-ij]quinolin-6-one-6-oxime-O-sulfonic acid potassium salt Compound 4: 9-chloro-4,5-dihydro-2-(4-nitrophenyl)-6H-imidazo[4,5,1-ij]quinolin-6-one-6-oxime-O-sulfonic acid potassium salt Compound 5: 9-chloro-4,5-dihydro-2-(2-naphthyl)-6H-imidazo[4,5,1-ij]quinolin-6-one-6-oxime-O-sulfonic acid potassium salt Compound 6: 9-chloro-2-(3-furyl)-4,5-dihydro-6H-imidazo[4,5,1-ij]quinolin-6-one-6-oxime-O-sulfonic acid potassium salt Compound 7: 4,5-dihydro-2-phenyl-6H-imidazo-[4,5,1-ij]quinolin-6-one-6-oxime-O-sulfonic acid potassium salt Compound 8: 9-chloro-4,5-dihydro-2-phenyl-6H-imidazo[4,5,1-ij]quinolin-6-one-6-oxime-O-sulfonic acid potassium salt Compound 9: 4,5-dihydro-8-methoxy-2-phenyl-6H-imidazo[4,5,1-ij]quinolin-6-one-6-oxime-O-sulfonic acid potassium salt Compound 10: 9-chloro-2-(4-chlorophenyl)-4,5-dihydro-6H-imidazo[4,5,1-ij]quinolin-6-one-6-oxime-O-sulfonic acid potassium salt Compound 11: 9-chloro-4,5-dihydro-2-(2-penten-3-yl)-6H-imidazo[4,5,1-ij]quinolin-6-one-6-oxime-O-sulfonic acid potassium salt Compound 12: 9-chloro-4,5-dihydro-2-(2-phenylethyl)-6H-imidazo[4,5,1-ij]quinolin-6-one-6-oxime-O-sulfonic acid potassium salt Compound 13: 9-chloro-4,5-dihydro-2-(3-phenylpropyl)-6H-imidazo[4,5,1-ij]quinolin-6-one-6-oxime-O-sulfonic acid potassium salt Compound 14: 9-chloro-4,5-dihydro-2-(2-thienylmethyl)-6H-imidazo[4,5,1-ij]quinolin-6-one-6-oxime-O-sulfonic acid potassium salt Compound 15: 9-chloro-2-cyclohexyl-4,5-dihydro-6H-imidazo[4,5,1-ij]quinolin-6-one-6-oxime-O-sulfonic acid potassium salt Compound 16: 9-chloro-2-(4-fluorophenyl)-4,5-dihydro-6H-imidazo[4,5,1-ij]quinolin-6-one-6-oxime-O-sulfonic acid potassium salt Compound 17: 9-chloro-2-(2,4-dichlorophenyl)-4,5-dihydro-6H-imidazo[4,5,1-ij]quinolin-6-one-6-oxime-O-sulfonic acid potassium salt Compound 18: 9-chloro-2-[4-(N,N-diethylamino)-phenyl]-4,5-dihydro-6H-imidazo[4,5,1-ij]quinolin-6-one-6-oxime-O-sulfonic acid potassium salt Compound 19: 9-chloro-4,5-dihydro-2-(1-naphthyl)-6H-imidazo[4,5,1-ij]quinolin-6-one-6-oxime -O-sulfonic acid potassium salt Compound 20: 2-(5-bromothien-2-yl)-9-chloro-4,5-dihydro-6H-imidazo[4,5,1-ij]quinolin-6-one-6-oxime-O-sulfonic acid potassium salt Compound 21: 9-chloro-4,5-dihydro-2-thienyl-6H-imidazo[4,5,1-ij]quinolin-6-one-6-oxime-O-sulfonic acid potassium salt Compound 22: 8-chloro-4,5-dihydro-2-phenyl-6H-imidazo[4,5,1-ij]quinolin-6-one-6-oxime-O-sulfonic acid potassium salt Compound 23: 8-chloro-2-cyclohexyl-4,5-dihydro-6H-imidazo[4,5,1-ij]quinolin-6-one-6-oxime-O-sulfonic acid potassium salt

TABLE 1

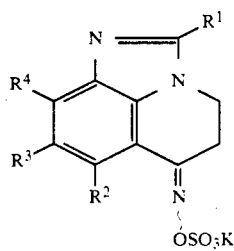

| Compound | 1 | 2 | 3 | 4 | 5 |
|---|---|---|---|---|---|

TABLE 1-continued

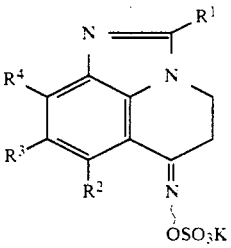

| R¹ | -CH₂-C₆H₅ | -CH(CH₃)CH₂CH₃ | cyclohexenyl | -C₆H₄-NO₂ | 2-naphthyl |
|---|---|---|---|---|---|
| R² | H | H | H | H | H |
| R³ | H | H | H | H | H |
| R⁴ | Cl | Cl | Cl | Cl | Cl |
| Compound | 6 | 7 | 8 | 9 | 10 |

| R¹ | 3-methylfuryl | phenyl | phenyl | phenyl | 4-Cl-phenyl |
|---|---|---|---|---|---|
| R² | H | H | H | H | H |
| R³ | H | H | H | OCH₃ | H |
| R⁴ | Cl | H | Cl | H | Cl |
| Compound | 11 | 12 | 13 | 14 | 15 |

| R¹ | -C(CH₃)=CH-CH₃ | -CH₂CH₂-C₆H₅ | -CH₂CH₂CH₂-C₆H₅ | -CH₂-thienyl | cyclohexyl |
|---|---|---|---|---|---|
| R² | H | H | H | H | H |
| R³ | H | H | H | H | H |
| R⁴ | Cl | Cl | Cl | Cl | Cl |
| Compound | 16 | 17 | 18 | 19 | 20 |

| R¹ | 4-F-phenyl | 2,4-diCl-phenyl | 4-N(C₂H₅)₂-phenyl | 1-naphthyl | 5-Br-thienyl |
|---|---|---|---|---|---|
| R² | H | H | H | H | H |
| R³ | H | H | H | H | H |
| R⁴ | Cl | Cl | Cl | Cl | Cl |
| Compound | 21 | 22 | 23 | | |

| R¹ | thienyl | phenyl | cyclohexyl |
|---|---|---|---|
| R² | H | H | H |
| R³ | H | Cl | Cl |
| R⁴ | Cl | H | H |

As regards oxime-O-sulfonic acid moieties, these representative compounds are shown as potassium salts. These moieties can also be made into free acids or other organic or inorganic salts.

To demonstrate the utility of the compounds of the present invention, data on diuretic and antihypertensive activities as well as acute toxicity of representative compounds are shown below.

EXPERIMENTAL EXAMPLE 1

Diuretic activity in dogs

Mongrel dogs weighing 7 to 20 kg were fasted overnight. The animals were anesthesized with pentobarbital (30 mg/kg body weight, i.v.) with ventilation, and physiological saline solution was continuously infused into femoral vein via catheter at the rate of 0.15 ml/kg/min. The animals were then laparotomized and left urethra was cannulated to collect urine in 10-minute periods. Compounds to be tested were administered intravenously and the changes in urine output was recorded. Percent increase in urine output was calculated by the formula given below:

Increase in urine output = (Urine output in the 90 minute period after the administration of the compound) − [(Urine output in the 30-minute period before administration) × 3]

Percent increase in urine output = (Increase in urine output by the tested compound) ÷ (Increase in urine output by furosemide) × 100

The results are shown below:

TABLE 2

| Compound | Dose (μg/kg) | Percent increase in urine output |
| --- | --- | --- |
| 1 | 100 | 480 |
| 2 | 100 | 293 |
| 3 | 100 | 384 |
| 4 | 100 | 346 |
| 5 | 100 | 420 |
| 6 | 100 | 420 |
| 7 | 100 | 193 |
| 8 | 100 | 391 |
| 9 | 100 | 124 |
| 10 | 100 | 414 |
| 11 | 100 | 618 |
| 12 | 100 | 537 |
| 13 | 100 | 435 |
| 14 | 100 | 351 |
| 15 | 100 | 616 |
| 16 | 100 | 302 |
| 17 | 100 | 302 |
| 18 | 100 | 322 |
| 19 | 100 | 607 |
| 20 | 100 | 574 |
| 21 | 100 | 603 |
| 22 | 100 | 297 |
| 23 | 100 | 330 |
| Furosemide | 100 | 100 |

All of the compounds of the present invention represented significant diuretic activities.

EXPERIMENTAL EXAMPLE 2

Hypotensive action in DOCA-salt mice

In order to obtain hypertensive animals, uninephrectomized ICR mice were subcutaneously administered 6 mg of deoxycorticosterone acetate (DOCA) twice a week, and given 1% NaCl aqueous solution as drinking water. Compounds to be tested were orally administered to groups of these mice, each group consisting 5 to 6 animals. Blood pressure was measured before and 6 hours after the administration with a plethysmograph.

The results are shown below.

TABLE 3

| Compound | Dose (mg/kg) | Blood pressure (mmHg) Before | After |
| --- | --- | --- | --- |
| 8 | 10 | 149 | 133 |

TABLE 3-continued

| Compound | Dose (mg/kg) | Blood pressure (mmHg) Before | After |
| --- | --- | --- | --- |
| 10 | 10 | 156 | 131 |

Significant hypotensive activities were observed for all of tested compounds.

EXPERIMENTAL EXAMPLE 3

Acute toxicity

Compounds to be tested were intraperitoneally administered to groups of ICR mice weighing 20 to 30 g. Each group consisted of 5 animals. Seven days after the administration, mortality was determined.

The results are shown below.

TABLE 4

| Compound | Dose (mg/kg) | Mortality |
| --- | --- | --- |
| 1 | 1000 | 0/5 |
| 2 | 500 | 0/5 |
| 5 | 500 | 0/5 |
| 6 | 1000 | 0/5 |
| 8 | 500 | 0/5 |

The doses of the experiment described above are considerably higher than those required for their pharmacological activities. Therefore, these compounds were deemed to have large margins for safety.

As demonstrated by the experimental examples described above, the compounds of the present invention possess significant diuretic and hypotensive activities, and also large margins for safety within the dose ranges to show these pharmacological activities. The compounds of the present invention further possess activities for antioedematous, the removal of ascites, the removal of uric acids and/or for the regulation of balances of electrolytes. Therefore, the compounds are of great use for the treatment and/or the prevention of hypertensions such as essential hypertension, renal hypertension, pernicious hypertension, etc., and/or oedemas such as congestive heart failure, renal oedema, hepatic oedema, gestosis, pregnant oedema, oedema by disturbances of peripheral circulation, etc., and/or ascites such as ascites seen in patient with abdominal tumor or liver cirrhosis. And it is presumed that the compounds of the present invention are effective to the diseases to which widely used diuretics have been effective, such as glaucoma, ulcer, renal urolithiasis, epilepsy, convulsion, myoclonus, etc.

4,5-dihydro-6H-imidazo-[4,5,1-ij]quinolin-6-one-6-oxime compounds, salts, solvates or solvates of said salts thereof, were tried to determine their diuretic activities in dogs using the method of experimental example 1. As the results, we found some of these compounds themselves had potent diuretic activity. For example, 9-chloro-4,5-dihydro-2-phenyl-6H-imidazo[4,5,1-ij]quinolin-6-one-6-oxime showed 353% of diuretic activity as furosemide's was 100%. In addition, these oxime compounds came out to be chemically stable and easily absorbed. These compounds achieved sufficient serum concentration and exhibited pharmaceutical effects after oral administration. Intraperitoneal administration of 1 g/kg of these oxime compounds to mice represented no mortality. Therefore when used in the same manner and in the same dose with oxime-O-sulfonic acid compounds, these oxime compounds may be of great use for the treatment and/or the prevention of hypertensions such as essential hypertension, renal hypertension, pernicious hypertension, etc., and/or oedemas such as congestive heart failure, renal oedema, hepatic oedema, gestosis, pregnant oedema, oedema by disturbances of peripheral circulation, etc., and/or ascites such as ascites seen in patient with abdominal tumor or liver cirrhosis.

The 4,5-dihydro-6H-imidazo[4,5,1-ij]quinolin-6-one-6-oxime-O-sulfonic acid compounds of the present invention represented by the formula (I) may form pharmaceutically acceptable salts with organic or inorganic bases. Typical examples of such salts of the compounds include pharmaceutically acceptable salts such as alkali metal salts such as sodium salts, potassium salts, etc.; alkaline earth metal salts such as calcium salts, etc.; salts of organic bases such as ammonium salts, benzylamine salts, diethylamine salts, etc.; salts of amino acids such as arginine salts, lysine salts, etc.

The 4,5-dihydro-6H-imidazo[4,5,1-ij]quinolin-6-one-6-oxime-O-sulfonic acid compounds of the present invention can be employed as pharmaceutical compositions, for example, in the form of pharmaceutical compositions containing the 4,5-dihydro-6H-imidazo[4,5,1-ij]quinolin-6-one-6-oxime-O-sulfonic acid compounds together with appropriate pharmaceutically acceptable carriers or medium such as sterilized water, edible oils, non-toxic organic solvents or non-toxic solubilizer such as glycerin or propylene glycol. They may be mixed with excipients, binders, lubricants, coloring agents, flavors, emulsifying agents or suspending agents such as Tween 80 or arabic gum to prepare tablets, capsules, powders, granules, subtilized granules, syrups, eye drops, suppositories, ointments, cataplasms, inhalants aqueous or oily solutions or emulsions or suspensions or lyophilized formulations. Further, they may be made into microcapsule formulations to improve the solubility, or into sustained release formulations. These preparations can be administered either orally or parenterally (such as intravenous administration, intramuscular administration, subcutaneous administration, intrarectal administration, percutaneous administration or permucosal administration; etc.). The amount of the administration of the compounds may be in the range of 0.01 to 1000 mg/day, preferably 0.1 to 100 mg/day when the preparation is tablets, capsules, powders, injections, suppositories, syrups, inharants or ointments, 0.01 μg to 10 mg/day, preferably 0.1 μg to 1 mg/day when the preparation is eye drops, and 1 to 10% composition when the preparation is ointments. And may also be adjusted according to the patient conditions and can be administered at a time or divided 2 to 6 times or by instillation, etc.

Hereafter the present invention will be described with references to the examples below but is not deemed to be limited thereof.

EXAMPLE 1

Preparation of 9-chloro-4,5-dihydro-2-phenyl-6H-imidazo[4,5,1-ij]quinolin-6-one-6-oxime-O-sulfonic acid potassium salt (compound 8)

Step 1

A mixture of 3-(3-chloro-2-nitrophenylamino)propionic acid (21.5 g), which was synthesized according to the method of Giovanni Pappalardo et al. (Ann. Chim. (Rome), 55, 182 (1965)), phosphorus pentoxide (37.0 g) and toluene (160 ml) was refluxed for 90 minutes. After cooling, toluene was removed in vacuo. The residue was washed with ether to give 7-chloro-2,3-dihydro-8-nitro-4(1H)-quinolinone (yield 10.0 g).

Melting point: 197.1°–198.9° C.

IR (KBr, cm$^{-1}$): 1671, 1604, 1524, 1267.

NMR (CDCl$_3$, ppm): 2.75 (2H, t), 3.73 (2H, dt), 6.33 (1H, b), 6.83 (1H, d), 7.94 (1H, d).

Step 2

A mixture of the product of Step 1 (10.0 g), tin(II) chloride dihydrate (60.0 g) and conc. hydrochloric acid (120 ml) was stirred for 2 hours at 30° C. Under cooling condition, reaction mixture was added 20% sodium hydroxide to be weak alkaline, then extracted with ethyl acetate (500 ml). The organic layer was washed with saturated aqueous NaCl solution and dried over anhydrous sodium sulfate. Ethyl acetate was removed in vacuo and the residue was washed with ether to give 8-amino-7-chloro-2,3-dihydro-4(1H)-quinolinone (yield 5.2 g).

Melting point: 105.2°–108.8° C.

IR (KBr, cm$^{-1}$): 1639, 1603, 1228, 1193.

NMR (CDCl$_3$, ppm): 2.68 (2H, t), 3.61 (4H, m), 4.47 (1H, b), 6.76 (1H, d), 7.41 (1H, d).

Step 3

A mixture of the product of Step 2 (15.0 g), benzaldehyde (9.5 g), methanol (150 ml) and 1M hydrochloric acid (0.2 ml) was stirred for 1 hour at room temperature. To the reaction mixture were added dichloromethane (100 ml) and silica gel (150 ml). After removing methanol and dichloromethane in vacuo, the residue was heated for 4 hours at 90° C. After cooling, the residue was subjected to silica gel column chromatography using dichloromethane to give 9-chloro-4,5-dihydro-2-phenyl-6H-imidazo[4,5,1-ij]quinoline-6-one (yield 13.0 g).

Melting point: 206.2°–208.7° C.

IR (KBr, cm$^{-1}$): 1697, 1594, 1341, 1126, 702.

NMR (DMSO-d$_6$, ppm): 3.10 (2H, t), 4.80 (2H, t), 7.41 (1H, d), 7.55–7.65 (4H, m), 7.80–8.01 (2H, m).

Step 4

To a mixture of the product of Step 3 (12.0 g), methanol (140 ml) and dichloromethane (140 ml) was added hydroxylamine-O-sulfonic acid (7.2 g) with stirring at room temperature. After stirring for 30 minutes at room temperature, to the reaction mixture was added aqueous potassium carbonate solution (8.8 g in 10 ml of water) at a time, and stirred for another 2 hours at room temperature. The formed precipitate was separated by filtration and extracted with hot methanol. After cooling the extract, formed precipitate was separated by filtration to give 9-chloro-4,5-dihydro-2-phenyl-6H-imidazo[4,5,1-ij]quinoline-6-one-6-oxime-O-sulfonic acid potassium salt (yield 13.0 g).

Melting point: 229.5° C. (decomposition).

IR (KBr, cm$^{-1}$): 1271, 1246, 1063, 826, 667.

NMR (DMSO-d$_6$, ppm): 3.20 (2H, t), 4.56 (2H, t), 7.35 (1H, d), 7.53–7.64 (4H, m), 7.92–8.03 (2H, m).

EXAMPLE 2

Preparation of 9-chloro-4,5-dihydro-2-phenyl-6H-imidazo[4,5,1-ij]quinoline-6-one-6-oxime-O-sulfonic acid potassium salt (compound 8)

Step 1

To an ethanol solution of 9-chloro-4,5-dihydro-2-phenyl-6H-imidazo[4,5,1-ij]quinolin-6-one (18.0 g in 200 ml of ethanol) obtained in a manner similar to Step 3 of Example 1 was added hydroxylamine hydrochloride (8.8 g) and pyridine (13.0 g), and the mixture was refluxed for 1 hour. Ethanol was removed in vacuo and the residue was added ethyl acetate (800 ml). The organic layer was washed with successive water and saturated aqueous NaCl solution. After drying over anhydrous sodium sulfate, ethyl acetate was removed in vacuo and the residue was purified by silica gel column chromatography using a hexane-ethyl acetate mixture (3:1) to give 9-chloro-4,5-dihydro-2-phenyl-6H-imidazo[4,5,1-ij]quinolin-6-one-6-oxime (yield 13.0 g).

Melting point: 251.0°–252.5° C.

IR (KBr, cm$^{-1}$): 3140, 2860, 1447, 1372, 1143, 1020.

NMR (DMSO-d$_6$, ppm): 3.18 (2H, t), 4.54 (2H, t), 7.30 (1H, d), 7.51 (1H, d), 7.50–7.71 (3H, m), 7.82–8.04 (2H, m), 11.60 (1H, s).

Step 2

The product of Step 1 (13.0 g) was dissolved in the mixed solvent of dichloromethane (100 ml) and N,N-dimethylformamide (20 ml), and was added sulfur trioxide-pyridine complex (14.0 g), then stirred for 24 hours at room temperature. To the reaction mixture was added methanol (150 ml), and then aqueous potassium carbonate solution (15.0 g in 10 ml of water) at a time. After stirring for 3 hours at room temperature, dichloromethane, methanol and N,N-dimethylformamide were removed in vacuo, then the residue was purified by silica gel column chromatography using a dichloromethane-methanol mixture (4:1) to give 9-chloro-4,5-dihydro-2-phenyl-6H-imidazo[4,5,1-ij]quinolin-6-one-6-oxime-O-sulfonic acid potassium salt (yield 8.0 g), of which melting point, IR and NMR spectra were completely identical to those of the product of Example 1.

EXAMPLE 3

Preparation of 8-chloro-4,5-dihydro-2-phenyl-6H-imidazo[4,5,1-ij]quinoline-6-one-6-oxime-O-sulfonic acid potassium salt (compound 22)

Step 1

Starting from 3-(4-chloro-2-nitrophenylamino)propionic acid (40.0 g), phosphorus pentoxide (70.0 g) and toluene (300 ml), 6-chloro-2,3-dihydro-8-nitro-4(1H)-quinolinone (yield 25.0 g) was obtained in a manner similar to Step 1 of Example 1.

Melting point: 132.5°–135.0° C.

IR (KBr, cm$^{-1}$): 3391, 1678, 1618, 1509, 1409, 1258.

NMR (CDCl$_3$, ppm): 2.81 (2H, t), 3.80 (2H, dt), 8.11–8.37 (1H, b), 8.13 (1H, d), 8.35 (1H, d).

Step 2

Starting from the product of Step 1 (25.0 g), tin(II) chloride dihydrate (150.0 g) and conc. hydrochloric acid (300 ml), 8-amino-6-chloro-2,3-dihydro-4(1H)-quinolinone (yield 10.0 g) was obtained in a manner similar to Step 2 of Example 1.

Melting point: 142.0°–144.3° C.

IR (KBr, cm$^{-1}$): 1654, 1507, 1340, 1266, 1154.

NMR (CDCl$_3$, ppm): 2.68 (2H, t), 3.59 (2H, t), 3.35–3.71 (2H, b), 4.49–5.07 (1H, b), 6.81 (1H, d), 7.42 (1H, d).

Step 3

A mixture of the product of Step 2 (10.0 g), trimethyl orthobenzoate (13 ml), p-toluenesulfonic acid monohydrate (1.0 g) and toluene (150 ml) was refluxed for 30 minutes. After cooling, formed precipitate was separated by filtration and washed with ether to give 8-chloro-4,5-dihydro-2-phenyl-6H-imidazo[4,5,1-ij]quinolin-6-one (yield 12.0 g).

Melting point: 233.6°–234.9° C.

IR (KBr, cm$^{-1}$): 1676, 1453, 1303, 1216.

NMR (CDCl$_3$, ppm): 3.13 (2H, t), 4.73 (2H, t), 7.53–7.60 (3H, m), 7.72 (1H, d), 7.82–7.92 (2H, m), 7.97 (1H, d).

Step 4

Starting from the product of Step 3 (10.0 g) and hydroxylamine-O-sulfonic acid (6.0 g), 8-chloro-4,5-dihydro-2-phenyl-6H-imidazo[4,5,1-ij]quinolin-6-one-6-oxime-O-sulfonic acid potassium salt (yield 11.0 g) was obtained in a manner similar to Step 4 of Example 1.

Melting point: 240.0°–250.0° C.

IR (KBr, cm$^{-1}$): 1267, 1066, 830, 651.

NMR (DMSO-d$_6$, ppm): 3.19 (2H, t), 4.54 (2H, t), 7.49 (1H, d), 7.55–7.62 (3H, m), 7.79 (1H, d), 7.90–7.96 (2H, m).

EXAMPLE 4

Preparation of 9-chloro-4,5-dihydro-6H-imidazo[4,5,1-ij]quinolin-6-one-6-oxime-O-sulfonic acid potassium salt

Step 1

A mixture of 8-amino-7-chloro-2,3-dihydro-4(1H)-quinolinone (10.0 g) obtained in a manner similar to Step 2 of Example 1, trimethyl orthoformate (11 ml), p-toluenesulfonic acid monohydrate (1.0 g) and toluene (100 ml) was refluxed for 1 hour. After cooling, formed precipitate was separated by filtration and washed with ether to obtain 9-chloro-4,5-dihydro-6H-imidazo[4,5,1-ij]quinolin-6-one (yield 8.5 g).

Melting point: 224.0°–230.0° C.

IR (KBr, cm$^{-1}$): 3106, 1686, 1593, 1349, 1188, 1121.

NMR (DMSO-d$_6$, ppm): 3.06 (2H, t), 4.67 (2H, t), 7.39 (1H, d), 7.58 (1H, d), 8.51 (1H, s).

Step 2

Starting from the product of Step 1 (8.0 g) and hydroxylamine-O-sulfonic acid (4.5 g), 9-chloro-4,5-dihydro-6H-imidazo[4,5,1-ij]quinolin-6-one-6-oxime-O-sulfonic acid potassium salt (yield 8.0 g) was obtained in a manner similar to Step 4 of Example 1.

Melting point: 247.5° C. (decomposition).

IR (KBr, cm$^{-1}$): 3531, 3484, 3110, 1283, 1240, 1064, 821.

NMR (DMSO-d$_6$, ppm): 3.15 (2H, t), 4.40 (2H, t), 7.32 (1H, d), 7.54 (1H, d), 8.40 (1H, s).

EXAMPLE 5

Preparation of
9-chloro-2-(4-chlorophenyl)methyl-4,5-dihydro-6H-imidazo[4,5,1-ij]quinolin-6-one-6-oxime-O-sulfonic acid potassium salt

Step 1

A mixture of 8-amino-7-chloro-2,3-dihydro-4(1H)-quinolin (9.0 g) obtained in a manner similar to Step 2 of Example 1, 4-chlorophenylacetic acid (40.0 g) and 4M hydrochloric acid (150 ml) was refluxed for 24 hours. After cooling, the resulting solution was extracted with ether (600 ml). The organic layer was washed with successive 1M aqueous NaOH solution and water. After drying over anhydrous sodium sulfate, ether was removed in vacuo and the residue was purified by silica gel column chromatography using dichloromethane, then crystalized from a dichloromethane-hexane mixture to give 9-chloro-2-(4-chlorophenyl)methyl-4,5-dihydro-6H-imidazo[4,5,1-ij]quinolin-6-one (yield 8.0 g).

Melting point: 166.6°–167.4° C.

IR (KBr, cm$^{-1}$): 1694, 1596, 1125, 1088.

NMR (CDCl$_3$, ppm): 2.97 (2H, t), 4.24 (2H, t), 4.38 (2H, s), 7.27 (4H, d), 7.33 (1H, d), 7.64 (1H, d).

Step 2

Starting from the product of Step 1 (8.0 g) and hydroxylamine-O-sulfonic acid (5.0 g), 9-chloro-2-(4-chlorophenyl)methyl-4,5-dihydro-6H-imidazo[4,5,1-ij]quinolin-6-one-6-oxime-O-sulfonic acid potassium salt (yield 7.5 g) was obtained in a manner similar to Step 4 of Example 1.

Melting point: 216.4° C. (decomposition).

IR (KBr, cm$^{-1}$): 1287, 1249, 1138, 1123, 1065.

NMR (DMSO-d$_6$, ppm): 3.12 (2H, t), 4.27 (2H, t), 4.34 (2H, s), 7.26 (1H, d), 7.37 (4H, s), 7.49 (1H, d).

EXAMPLE 6

Preparation of
9-chloro-4,5-dihydro-2-(2-thienyl)-6H-imidazo[4,5,1-ij]quinolin-6-one-6-oxime-O-sulfonic acid sodium salt

Step 1

Starting from 8-amino-7-chloro-2,3-dihydro-4(1H)-quinolinone (15.0 g) obtained in a manner similar to Step 2 of Example 1 and 2-thiophenaldehyde (9 ml), 9-chloro-4,5-dihydro-2-(2-thienyl)-6H-imidazo[4,5,1-ij]quinolin-6-one (yield 13.0 g) was obtained in a manner similar to Step 3 of Example 1.

Melting point: 251.6°–253.8° C.

IR (KBr, cm$^{-1}$): 1696, 1677, 1597, 1464, 1128.

NMR (DMSO-d$_6$, ppm): 3.13 (2H, t), 4.90 (2H, t), 7.26–7.35 (1H, m), 7.37 (1H, d), 7.56 (1H, d), 7.87–7.93 (2H, m).

Step 2

To a mixture of the product of Step 1 (13.0 g), methanol (150 ml) and dichloromethane (150 ml) was added hydroxylamine-O-sulfonic acid (7.7 g) with stirring at room temperature. After stirring for 30 minutes at room temperature, to the reaction mixture was added aqueous sodium carbonate solution (7.2 g in 10 ml of water) at a time. After stirring for another 2 hours at room temperature, dichloromethane and methanol were removed in vacuo, then the residue was purified by silica gel column chromatography using a dichloromethane-methanol mixture (4:1) to give 9-chloro-4,5-dihydro-2-(2-thienyl)-6H-imidazo[4,5,1-ij]quinolin-6-one-6-oxime-O-sulfonic acid sodium salt (yield 9.1 g).

Melting point: 233.3° C. (decomposition).

IR (KBr, cm$^{-1}$): 1552, 1469, 1297, 1232, 1072.

NMR (DMSO-d$_6$, ppm): 3.20 (2H, t), 4.64 (2H, t), 7.26–7.57 (3H, m), 7.87 (2H, d).

EXAMPLE 7

Preparation of
2-(4-bromophenyl)-9-chloro-4,5-dihydro-6H-imidazo[4,5,1-ij]quinolin-6-one-6-oxime-O-sulfonic acid potassium salt

Step 1

Starting from 8-amino-7-chloro-2,3-dihydro-4(1H)-quinolinone (15.0 g) obtained in a manner similar to Step 2 of Example 1 and 4-bromobenzaldehyde (17.0 g), 9-chloro-2-(4-bromophenyl)-4,5-dihydro-6H-imidazo[4,5,1-ij]quinolin-6-one (yield 15.0 g) was obtained in a manner similar to Step 3 of Example 1.

Melting point: 177.4°–184.5° C.

IR (KBr, cm$^{-1}$): 1694, 1600, 1590, 1129.

NMR (DMSO-d$_6$, ppm): 3.09 (2H, t), 4.80 (2H, t), 7.42 (1H, d), 7.60 (1H, d), 7.80 (2H, d), 7.96 (2H, d).

Step 2

To a solution of the product of Step 1 (15.0 g) in ethanol (150 ml) was added hydroxylamine hydrochloride (5.5 g) and pyridine (6.0 g), and the mixture was refluxed for 1 hour. The resulting mixture was poured into water (500 ml), then formed precipitate was separated by filtration, washed with water and dried to give 2-(4-bromophenyl)-9-chloro-4,5-dihydro-6H-imidazo[4,5,1-ij]quinolin-6-one-6-oxime (yield 11.0 g).

Melting point: >250° C.

IR (KBr, cm$^{-1}$): 3180, 2865, 1403, 1142, 1011, 920.

NMR (DMSO-d$_6$, ppm): 3.18 (2H, t), 4.53 (2H, t), 7.30 (1H, d), 7.50 (1H, d), 7.78 (2H, d), 7.93 (2H, d), 11.59 (1H, s).

Step 3

To a solution of the product of Step 2 (8.0 g) in dichloromethane (100 ml) and N,N-dimethylformamide (25 ml) was added sulfur trioxide-pyridine complex (7.0 g), then stirred for 24 hours at room temperature. To the reaction mixture was added methanol (100 ml), and then aqueous potassium carbonate solution (7.0 g in 10 ml of water) at a time with stirring. After stirring for 3 hours at room temperature, dichloromethane, methanol and N,N-dimethylformamide were removed in vacuo, then the residue was purified by silica gel column chromatography using a dichloromethane-methanol mixture (4:1) to give 2-(4-bromophenyl)-9-chloro-4,5-dihydro-6H-imidazo[4,5,1-ij]quinolin-6-one-6-oxime-O-sulfonic acid potassium salt (yield 5.5 g).

Melting point: 224.6° C. (decomposition).

IR (KBr, cm$^{-1}$): 1272, 1242, 1065, 831.

NMR (DMSO-d$_6$, ppm): 3.18 (2H, t), 4.54 (2H, t), 7.36 (1H, d), 7.56 (1H, d), 7.79 (2H, d), 7.94 (2H, d).

EXAMPLE 8

Preparation of 4,5-dihydro-8-hydroxy-2-phenyl-6H-imidazo[4,5,1-ij]quinolin-6-one-6-oxime-O-sulfonic acid potassium salt

Step 1

Starting from 3-(4-methoxy-2-nitrophenylamino)propionic acid (50.0 g), phosphorus pentoxide (80.0 g) and toluene (350 ml), 2,3-dihydro-6-methoxy-8-nitro-4(1H)-quinolinone (yield 20.0 g) was obtained in a manner similar to Step 1 of Example 1.

Melting point: 161.0°–162.3° C.

IR (KBr, cm$^{-1}$): 3369, 1685, 1573, 1515, 1177.

NMR (DMSO-d$_6$+CDCl$_3$, ppm): 2.71 (2H, t), 3.77 (2H, t), 3.81 (3H, s), 7.71 (1H, d), 7.84 (1H, d), 8.26 (1H, b).

Step 2

Starting from the product of Step 1 (20.0 g), tin(II) chloride dihydrate (120.0 g) and conc. hydrochloric acid (300 ml), 8-amino-6-methoxy-2,3-dihydro-4(1H)-quinolinone (yield 10.0 g) was obtained in a manner similar to Step 2 of Example 1.

Melting point: 107.4°–109.6° C.

IR (KBr, cm$^{-1}$): 3387, 1648, 1637, 1509, 1160.

NMR (DMSO-d$_6$, ppm): 2.66 (2H, t), 3.46 (3H, b), 3.57 (2H, t), 3.75 (3H, s), 6.52 (1H, d), 6.91 (1H, d).

Step 3

Starting from the product of Step 2 (10.0 g) and trimethyl orthobenzoate (15 ml), 4,5-dihydro-8-methoxy-2-phenyl-6H-imidazo[4,5,1-ij]quinolin-6-one (yield 12.5 g) was obtained in a manner similar to Step 3 of Example 2.

Melting point: 161.4°–163.0° C.

IR (KBr, cm$^{-1}$): 1690, 1490, 1385, 1375, 1155.

NMR (CDCl$_3$, ppm): 3.10 (2H, t), 3.90 (3H, s), 4.69 (2H, t), 7.33 (1H, d), 7.49–7.56 (3H, m), 7.54 (1H, d), 7.80–7.88 (2H, m).

Step 4

Starting from the product of Step 3 (11.0 g) and hydroxylamine hydrochloride (5.5 g), 4,5-dihydro-8-methoxy-2-phenyl-6H-imidazo[4,5,1-ij]quinolin-6-one-6-oxime (yield 9.0 g) was obtained in a manner similar to Step 2 of Example 7.

Melting point: 234.9°–238.4° C.

IR (KBr, cm$^{-1}$): 3130, 1490, 1370, 1130, 1020.

NMR (DMSO-d$_6$, ppm): 3.19 (3H, s), 3.26 (2H, t), 4.66 (2H, t), 7.29–7.36 (2H, m), 7.71–7.77 (3H, m), 7.98–8.06 (2H, m), 12.01 (1H, bs).

Step 5

Under nitrogen atmosphere and cooling at −70° C. with stirring, to a solution of the product of Step 4 (7.5 g) in dichloromethane (300 ml) was added dropwise the solution of boron tribromide (11 ml) in dichloromethane (200 ml) over 30 minutes, then the mixture was gradually warmed to room temperature and stirred for 24 hours. The resulting mixture was poured into water (500 ml) and extracted with ethyl acetate (1000 ml). The organic layer was washed with saturated aqueous NaCl solution and dried over anhydrous sodium sulfate. Dichloromethane and ethyl acetate were removed in vacuo and the residue was purified by silica gel column chromatography using a dichloromethane-methanol mixture (19:1) to give 4,5-dihydro-8-hydroxy-2-phenyl-6H-imidazo[4,5,1-ij]-quinolin-6-one-6-oxime (yield 6.5 g).

Melting point: 208.7° C. (decomposition).

IR (KBr, cm$^{-1}$): 1613, 1479, 1460, 1378, 1138.

NMR (DMSO-d$_6$, ppm): 3.23 (2H, t), 4.63 (2H, t), 7.16 (1H, d), 7.30 (1H, d), 7.72–8.03 (5H, m), 9.80–10.20 (1H, b), 11.97 (1H, bs).

Step 6

Under nitrogen atmosphere and cooling at 0° C. with stirring, to a solution of the product of Step 5 (6.0 g) in anhydrous N,N-dimethylformamide (150 ml) was added dropwise over 30 minutes the solution of sulfur trioxide-N,N-dimethylformamide complex in N,N-dimethylformamide which was prepared from trimethylsilyl chlorosulfonate (15 ml) and N,N-dimethylformamide (100 ml), then the mixture was stirred for 5 hours at room temperature. To the reaction mixture was added aqueous potassium carbonate solution (9.0 g in 10 ml of water) at a time, and stirred for 3 hours at room temperature. N,N-dimethylformamide was removed in vacuo, and the residue was crystalized from methanol to give 4,5-dihydro-8-hydroxy-2-phenyl-6H-imidazo[4,5,1-ij]-quinolin-6-one-6-oxime-O-sulfonic acidpotassium salt (yield 3.5 g).

Melting point: 208.2° C. (decomposition).

IR (KBr, cm$^{-1}$): 1288, 1275, 1224, 1143, 1058.

NMR (DMSO-d$_6$, ppm): 3.22 (2H, t), 4.62 (2H, t), 7.16 (1H, d), 7.35 (1H, d), 7.71–8.00 (5H, m), 9.90–10.43 (1H, b).

EXAMPLE 9

Preparation of 7,8-dichloro-4,5-dihydro-2-phenyl-6H-imidazo[4,5,1-ij]quinolin-6-one-6-oxime-O-sulfonic acid potassium salt

Step 1

Starting from 3-(4,5-dichloro-2-nitrophenylamino)propionic acid (40.0 g), phosphorus pentoxide (70.0 g) and toluene (300 ml), 5,6-dichloro-2,3-dihydro-8-nitro-4(1H)-quinolinone (10.0 g) was obtained in a manner similar to Step 1 of Example 1.

Melting point: 174.8°–176.5° C.

IR (KBr, cm$^{-1}$): 3328, 1686, 1610, 1241, 1213.

NMR (DMSO-d$_6$, ppm): 2.74 (2H, t), 3.72 (2H, dt), 8.41 (1H, s), 8.98 (1H, b).

Step 2

Starting from the product of Step 1 (10.0 g), tin(II) chloride dihydrate (60.0 g) and conc. hydrochloric acid (120 ml), 8-amino-5,6-dichloro-2,3-dihydro-4(1H)-quinolinone (yield 5.0 g) was obtained in a manner similar to Step 2 of Example 1.

Melting point: 180.7°–183.4° C.

IR (KBr, cm$^{-1}$): 3374, 1654, 1648, 1506, 1253.

NMR (DMSO-d$_6$, ppm): 2.54 (2H, t), 3.49 (2H, t), 4.50–5.10 (2H, b), 6.00–6.12 (1H, b), 6.78 (1H, s).

Step 3

Starting from the product of Step 2 (5.0 g) and trimethyl orthobenzoate (8 ml), 7,8-dichloro-4,5-dihydro-2-phenyl-6H-imidazo[4,5,1-ij]quinolin-6-one (yield 4.8 g) was obtained in a manner similar to Step 3 of Example 3.

Melting point: 194.5°–200.6° C.

IR (KBr, cm$^{-1}$): 1686, 1483, 1444, 1294, 1282, 1121.

NMR (DMSO-d$_6$, ppm): 3.12 (2H, t), 4.77 (2H, t), 7.56–7.64 (3H, m), 7.90–8.01 (2H, m), 8.23 (1H, s).

Step 4

Starting from the product of Step 3 (4.5 g) and hydroxylamine-O-sulfonic acid (2.5 g), 7,8-dichloro-4,5-dihydro-2-phenyl-6H-imidazo[4,5,1-ij]quinolin-6-one-6-oxime-O-sulfonic acid potassium salt (yield 3.0 g) was obtained in a manner similar to Step 4 of Example 1.

Melting point: 219.8° C. (decomposition).

IR (KBr, cm$^{-1}$): 1277, 1249, 1063, 799, 655.

NMR (DMSO-$d_6$, ppm): 3.20 (2H, t), 4.52 (2H, t), 7.55–7.62 (3H, m), 7.89–7.95 (2H, m), 8.01 (1H, s).

Compounds of examples 10 to 115 are summarized in the following Tables 6 to 10 together with corresponding IR and NMR data (NMR data were generally measured in DMSO-$d_6$ except several data, which were measured in CDCl$_3$ and marked with asterisks(*)) and melting (or decomposition) points.

The methods by which these compounds are synthesized can be classified into eight groups as shown below.

TABLE 5

| Group | Synthetic method (representative example number) | Example number in Table 6 to 10 |
|---|---|---|
| A | 1 (Step 4) | 10–30, 32–42, 44–57 |
| B | 7 (Step 3) | 31, 43 |
| C | 7 (Step 2) | 58, 59 |
| D | 1 (Step 3) | 60–63, 69, 70, 72–74, 76–103 |
| E | 3 (Step 3) | 64–68 |
| F | 5 (Step 1) | 71, 75 |
| G | 1 (Step 2) | 104–109 |
| H | 1 (Step 1) | 110–115 |

TABLE 6

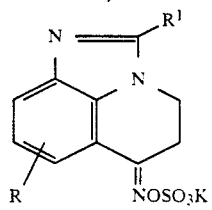

| Exp. No. | R$^1$ | R | IR(KBr, cm$^{-1}$) | NMR(DMSO-$d_6$, ppm) | M.P. (dec. °C.) |
|---|---|---|---|---|---|
| 10 | phenyl | H | 1260, 1240, 1055, 815 | 3.21(2H, t), 4.54(2H, t), 7.29(1H, t), 7.73(1H, d), 7.54–7.65(4H, m), 7.90–7.97(2H, m) | 225.7 |
| 11 | phenyl | 7-Cl | 1260, 1240, 1055, 815 | 3.19(2H, t), 4.51(2H, t), 7.30(1H, d), 7.54–7.65 (3H, m), 7.69(1H, d), 7.83–7.95(2H, m) | 230.1 |
| 12 | cyclohexyl | 8-Cl | 2932, 1287, 1235, 1068 | 1.15–2.11(10H, m), 2.71–3.21(1H, m), 3.13(2H, t), 4.31(2H, t), 7.40(1H, d), 7.63(1H, d) | 236.9 |
| 13 | phenylpropyl | 8-Cl | 1498, 1272, 1254, 1067, 823, 649 | 3.03(2H, t), 3.13(4H, m), 4.12(2H, t), 7.25(5H, m), 7.40(1H, d), 7.66(1H, d) | 233.5 |
| 14 | phenyl | 8-F | 1275, 1250, 1065, 865, 825 | 3.19(2H, t), 4.53(2H, t), 7.30(1H, dd), 7.50–7.62(4H, m), 7.86–8.23(2H, m) | 232.1 |
| 15 | phenyl | 8-Br | 1260, 1240, 1135, 1120, 1065, 825 | 3.19(2H, t), 4.54(2H, t), 7.54–7.66(4H, m), 7.90–8.01(3H, m) | 226.6 |
| 16 | phenyl | 8-I | 1270, 1245, 1060, 860, 820 | 3.18(2H, t), 4.54(2H, t), 7.57–8.43(7H, m) | 233.8 |
| 17 | phenyl | 8-CF$_3$ | 1345, 1275, 1265, 1240, 1105, 1060 | 3.23(2H, t), 4.59(2H, t), 7.57–7.65(3H, m), 7.78(1H, d), 7.92–8.03 (2H, m), 8.08(1H, d) | 223.5 |

TABLE 6-continued

[Structure: bicyclic system with N=C-R¹ and N-CH₂-CH₂-C(=NOSO₃K) with R substituent]

| Exp. No. | R¹ | R | IR(KBr, cm⁻¹) | NMR(DMSO-$d_6$, ppm) | M.P. (dec. °C.) |
|---|---|---|---|---|---|
| 18 | phenyl | 8-OCH₃ | 1245, 1125, 1060, 825 | 3.17(2H, t), 3.85(3H, s), 4.51(2H, t), 7.16(1H, d), 7.29(1H, d), 7.53–7.61 (3H, m), 7.88–7.95(2H, m) | 236.0 |
| 19 | phenyl | 9-CH₃ | 1240, 1060, 860, 825 | 2.61(3H, s), 3.17(2H, t), 4.50(2H, t), 7.11(1H, d), 7.45–7.62(4H, m), 7.89–8.01(2H, m) | 225.9 |
| 20 | –CH₂–phenyl | 9-Cl | 3070, 1273, 1248, 1064 | 3.10(2H, t), 4.26(2H, t), 4.33(2H, s), 7.13–7.41 (6H, m), 7.47(1H, d) | >250.0 |
| 21 | phenyl-O-ethyl | 9-Cl | 1598, 1284, 1237, 1066, 869 | 3.16(2H, t), 4.44(2H, t), 5.45(2H, s), 6.86–7.43(5H, m), 7.33(1H, d), 7.55(1H, d) | 188.5 |
| 22 | –CH₂-thienyl | 9-Cl | 1267, 1243, 1063, 825 | 3.12(2H, t), 4.29(2H, t), 4.55(2H, s), 6.97(1H, d), 7.28(1H, d), 7.38–7.45 (2H, m), 7.49(1H, d) | 210.4 |
| 23 | –n-C₈H₁₇ | 9-Cl | 2920, 1266, 1241, 1140, 1072, 866 | 0.73–1.20(3H, m), 1.16–1.54(10H, m), 1.63–1.93 (2H, m), 2.88(2H, t), 3.13(2H, t), 4.30(2H, t), 7.23(1H, d), 7.46(1H, d) | 177.0 |
| 24 | –CH₂CH₂CH₂-phenyl | 9-Cl | 1277, 1241, 1142, 1066, 829 | 3.03(2H, t), 2.85–3.34 (4H, m), 4.14(2H, t), 7.20–7.30(6H, m), 7.46(1H, d) | 185.0 |
| 25 | –CH₂CH₂CH₂-cyclohexyl | 9-Cl | 2923, 1260, 1140, 1069, 865 | 1.06–1.40(6H, m), 1.45–1.80(7H, m), 2.83–3.02(2H, m), 3.12(2H, t), 4.30(2H, t), 7.23(1H, d), 7.45(1H, d) | 238.1 |
| 26 | –CH₂CH₂OH | 9-Cl | 1654, 1648, 1273, 1241, 1062, 836 | 2.52–2.70(2H, m), 2.71 (2H, t), 3.51–3.88 (4H, m), 5.22–5.30 (1H, b), 7.30(2H, d) | 206.1 |
| 27 | –CH₂CH₂CH₂CH₂-phenyl | 9-Cl | 1282, 1271, 1253, 1140, 1071 | 1.88–2.34(2H, m), 2.74(2H, t), 2.89(2H, t), 3.12(2H, t), 4.26(2H, t), 7.19–7.32(6H, m), 7.45(1H, d) | 223.0 |
| 28 | –CH(CH₃)₂ | 9-Cl | 2976, 1293, 1215, 822 | 1.36(6H, d), 3.15(2H, t), 3.18–3.49(1H, m), 4.34 (2H, t), 7.25(1H, d), 7.48(1H, d) | 215.5 |
| 29 | –C(CH₃)₃ | 9-Cl | 2990, 1275, 1245, 1140, 1070 | 1.48(9H, s), 3.14(2H, t), 4.50(2H, t), 7.24(1H, d), 7.49(1H, d) | 228.9 |

TABLE 6-continued

[Structure: quinoline derivative with =N-R¹ substituent, R at position on ring, and =NOSO₃K group]

| Exp. No. | R¹ | R | IR(KBr, cm⁻¹) | NMR(DMSO-d₆, ppm) | M.P. (dec. °C.) |
|---|---|---|---|---|---|
| 30 | -CH(CH₂CH₃)(CH₂CH₃) (isobutyl-like, 2-methylpropyl branched) | 9-Cl | 2965, 1275, 1259, 1241, 1076 | 0.82(6H, t), 1.56-1.95 (4H, m), 2.68-3.04 (1H, m), 3.14(2H, t), 4.33(2H, t), 7.27(1H, d), 7.46(1H, d) | 201.0 |
| 31 | -CH(CH₃)(C₆H₅) | 9-Cl | 1276, 1241, 1144, 1065 | 1.72(3H, d), 2.74-3.26 (2H, m), 3.60-3.99 (1H, m), 4.16-4.69 (2H, m), 7.16-7.37 (6H, m), 7.48(1H, d) | 202.9 |
| 32 | -C(CH₃)=CH(CH₃)-CH₃ (2-methyl-2-butenyl-type) | 9-Cl | 1269, 1242, 1143, 1086, 859 | 1.02(3H, t), 1.91(3H, d), 2.64(2H, q), 3.13(2H, t), 4.37(2H, t), 6.15(1H, q), 7.27(1H, d), 7.48(1H, d) | 218.8 |
| 33 | -CH=CH-C₆H₅ (styryl with CH₃) | 9-Cl | 1245, 1229, 1143, 1128, 1120, 620 | 3.20(2H, t), 4.54(2H, t), 7.16-7.59(6H, m), 7.69-8.01(3H, m) | 200.0 |
| 34 | cyclopropyl | 9-Cl | 1298, 1227, 1068, 856, 824 | 1.03-1.20(4H, m), 2.01-2.40(1H, m), 31.6(2H, t), 4.41(2H, t), 7.20(1H, d), 7.41(1H, d) | 237.4 |
| 35 | cyclohexyl | 9-Cl | 2940, 2850, 1257, 1145, 1069 | 1.17-2.07(10H, m), 2.81-3.20(1H, m), 3.12(2H, t), 4.33(2H, t), 7.22(1H, d), 7.45(1H, d) | 240.0 |
| 36 | cyclohex-3-enyl | 9-Cl | 2940, 1283, 1273, 1255, 1139 | 1.67-2.44(6H, m), 3.00-3.30(1H, m), 3.15(2H, t), 4.36(2H, t), 5.78(2H, m), 7.26(1H, d), 7.50(1H, d) | 250.0 |
| 37 | cyclohex-1-enyl | 9-Cl | 1281, 1240, 1142, 1071, 860, 628 | 1.58-1.93(4H, m), 2.30-2.60(4H, m), 3.12(2H, t), 4.43(2H, t), 6.45-6.55(1H, m), 7.27(1H, d), 7.48(1H, d) | 250.0 |
| 38 | 2-chlorocyclohex-1-enyl | 9-Cl | 1276, 1241, 1144, 1067, 864 | 1.69-1.90(4H, m), 2.20-2.79(4H, m), 3.13(2H, t), 4.24(2H, t), 7.32(1H, d), 7.52(1H, d) | 225.1 |
| 39 | 4-fluorophenyl | 9-Cl | 1276, 1237, 1145, 1063, 843, 830 | 3.17(2H, t), 4.53(2H, t), 7.30-7.59(4H, m), 8.02(2H, dd) | 236.1 |
| 40 | 4-chlorophenyl | 9-Cl | 1301, 1228, 1069, 832, 625 | 3.19(2H, t), 4.55(2H, t), 7.35(1H, d), 7.57(1H, d), 7.66(2H, d), 8.01(2H, d) | 250.0 |

TABLE 6-continued

Structure:
8-position: N=C(R¹)–N (imidazoline fused)
4-position: =NOSO₃K
R at 6-position

| Exp. No. | R¹ | R | IR(KBr, cm⁻¹) | NMR(DMSO-d₆, ppm) | M.P. (dec. °C.) |
|---|---|---|---|---|---|
| 41 | 2-methylphenyl (CH₃) | 9-Cl | 1274, 1242, 1063, 858, 828 | 2.35(3H, s), 3.15(2H, t), 4.18(2H, t), 7.30–7.61(6H, m) | 221.8 |
| 42 | 4-OCH₃-phenyl | 9-Cl | 1295, 1263, 1232, 1069, 821 | 3.12(2H, t), 3.87(3H, s), 4.53(2H, t), 7.16(2H, d), 7.34(1H, d), 7.59(1H, d), 7.92(2H, d) | 250.0 |
| 43 | 4-NO₂-phenyl | 9-Cl | 1523, 1348, 1249, 1067, 861, 624 | 3.20(2H, t), 4.61(2H, t), 7.39(1H, d), 7.61(1H, d), 8.26(2H, d), 8.43(2H, d) | 231.1 |
| 44 | 4-N(C₂H₅)₂-phenyl | 9-Cl | 2985, 1608, 1465, 1272, 1243 | 1.15(6H, t), 3.17(2H, t), 3.21–3.67(4H, m), 4.52(2H, t), 6.81(2H, d), 7.27(1H, d), 7.48(1H, d), 7.78(2H, d) | 213.0 |
| 45 | 2,4-dichlorophenyl | 9-Cl | 1283, 1251, 1142, 1072, 822, 626 | 3.16(2H, t), 4.20(2H, t), 7.39(1H, d), 7.57–7.83 (3H, m), 7.90(1H, d) | 250.0 |
| 46 | 2-naphthyl | 9-Cl | 1283, 1232, 1066, 867 | 3.23(2H, t), 4.68(2H, t), 7.37(1H, d), 7.53–7.71 (3H, m), 7.94–8.32 (4H, m), 8.58(1H, s) | 240.0 |
| 47 | 1-naphthyl | 9-Cl | 1276, 1263, 1239, 1143, 1067, 861 | 3.15(2H, t), 4.22(2H, t), 7.41(1H, d), 7.57–7.97(5H, m), 8.00–8.27(3H, m) | 235.4 |
| 48 | 4-methoxy-1-naphthyl | 9-Cl | 1583, 1274, 1245, 1142, 1063 | 3.15(2H, t), 4.09(3H, s), 4.21(2H, t), 7.18(1H, d), 7.39(1H, d), 7.84(1H, d), 7.54–7.66(3H, m), 8.08–8.36(2H, m) | 200.0 |
| 49 | 3-furyl | 9-Cl | 1285, 1235, 1060, 890, 820 | 3.20(2H, t), 4.54(2H, t), 7.14(1H, s), 7.30(1H, d), 7.52(1H, d), 7.92(1H, d), 8.54(1H, s) | 255.2 |
| 50 | 2-furyl | 9-Cl | 1275, 1237, 1149, 1062, 825 | 3.21(2H, t), 4.68(2H, t), 6.81–6.91(1H, m), 7.33(1H, d), 7.38(1H, d), 7.55(1H, d), 8.03(1H, d) | 232.9 |

TABLE 6-continued

[Structure: bicyclic with N=CR¹ substituent, R group, and =NOSO₃K]

| Exp. No. | R¹ | R | IR(KBr, cm⁻¹) | NMR(DMSO-d₅, ppm) | M.P. (dec. °C.) |
|---|---|---|---|---|---|
| 51 | 3-methylthiophene | 9-Cl | 1275, 1235, 1065, 820 | 3.21(2H, t), 4.61(2H, t), 7.32(1H, d), 7.55(1H, d), 7.76(1H, d), 7.77(1H, d), 8.32(1H, dd) | 245.9 |
| 52 | 2-methylthiophene | 9-Cl | 1278, 1230, 1146, 1068, 821 | 3.18(2H, t), 4.65(2H, t), 7.23-7.33(1H, m), 7.30(1H, d), 7.53(1H, d), 7.83-7.88(2H, m) | 246.3 |
| 53 | 5-methyl-2-bromothiophene | 9-Cl | 1271, 1246, 1143, 1114, 1064, 618 | 3.20(2H, t), 4.62(2H, t), 7.33(1H, d), 7.41(1H, d), 7.53(1H, d), 7.69(1H, d) | 241.1 |
| 54 | 3-pyridyl | 9-Cl | 1295, 1245, 1060, 815 | 3.21(2H, t), 4.59(2H, t), 7.38(1H, d), 7.59(1H, d), 7.46-7.72(1H, m), 8.32-8.41(1H, m), 8.44(1H, d), 8.95(1H, dd) | 218.5 |
| 55 | 4-tetrahydropyranyl | 9-Cl | 2970, 2870, 1279, 1256, 1061, 616 | 1.70-2.10(4H, m), 3.13 (2H, t), 3.13-3.47 (1H, m), 3.30-3.80 (2H, m), 3.54-4.27 (2H, m), 4.36(2H, t), 7.24(1H, d), 7.46(1H, d) | 250.0 |
| 56 | 4-quinolyl | 9-Cl | 1273, 1242, 1064, 862, 828 | 3.17(2H, t), 4.34(2H, t), 7.45(1H, d), 7.65(1H, d), 7.75-8.04(2H, m), 7.90(1H, d), 8.13-8.67 (2H, m), 9.12(1H, d) | 250.0 |
| 57 | 5-methoxy-3-indolyl | 9-Cl | 1561, 1384, 1283, 1245, 1143, 1064 | 3.21(2H, t), 3.83(3H, s), 4.60(2H, t), 6.71-7.00 (1H, m), 7.31-7.48 (3H, m), 8.07-8.23 (2H, m), 11.50-11.95 (1H, b) | 203.5 |

TABLE 7

[Structure: bicyclic with N=CR¹ substituent, R group, and =NOH]

| Exp. No. | R¹ | R | IR(KBr, cm⁻¹) | NMR(DMSO-d₅, ppm) | M.P. (°C.) |
|---|---|---|---|---|---|
| 58 | —CH(CH₃)(phenyl) | 9-Cl | 3200, 3060, 2880, 1498, 1025, 922 | 1.72(3H, d), 2.87-3.12 (2H, m), 3.50-3.89 (1H, m), 4.16-4.67 (2H, m), 7.11-7.39 (6H, m), 7.41(1H, d), 11.50(1H, s) | 229.4-233.0 |

TABLE 7-continued

Structure:
```
       R¹
   N═══
        N
        │
        │
R       NOH
```

| Exp. No. | R¹ | R | IR(KBr, cm⁻¹) | NMR(DMSO-d₆, ppm) | M.P. (°C) |
|---|---|---|---|---|---|
| 59 | —⟨benzene⟩—NO₂ | 9-Cl | 1523, 1349, 1310, 1145, 930 | 3.20(2H, t), 4.60(2H, t), 7.35(1H, d), 7.54(1H, d), 8.24(1H, d), 8.44(2H, d), 11.6(1H, s) | 249.3–256.9 |

TABLE 8

Structure:
```
       R¹
   N═══
        N
        │
R       O
```

| Exp. No. | R¹ | R | IR(KBr, cm⁻¹) | NMR(DMSO-d₆, ppm) | M.P. (°C) |
|---|---|---|---|---|---|
| 60 | phenyl | H | 1690, 1680, 1475, 1440, 1340 | 3.10(2H, t), 4.78(2H, t), 7.35(1H, t), 7.55–7.64 (4H, m), 7.93–8.03(3H, m) | 115.9–117.1 |
| 61 | phenyl | 7-Cl | 1690, 1590, 1480, 1440, 1335 | 3.10(2H, t), 4.76(2H, t), 7.31(1H, d), 7.50–7.65 (3H, m), 7.86–8.01 (2H, m), 7.91(1H, d) | 182.4–184.0 |
| 62 | cyclohexyl | 8-Cl | 2930, 2850, 1683, 1286, 1214, 1115 | 1.14–2.12(10H, m), 2.74–3.12(1H, m), 3.06(2H, t), 4.57(2H, t), 7.44(1H, d), 7.91(1H, d) | 127.8–128.9 |
| 63 | —CH₂CH₂CH₂—phenyl | 8-Cl | 1692, 1498, 1277, 1210, 1117 | 2.99(2H, t), 3.18(4H, m), 4.43(2H, t), 7.27(5H, m), 7.44(1H, d), 7.92(1H, d) | 128.8–130.3 |
| 64 | phenyl | 8-F | 1690, 1675, 1445, 1300, 1105 | 3.12(2H, t), 4.79(2H, t), 7.37(1H, dd), 7.55–7.63 (3H, m), 7.84(1H, dd), 7.90–7.95(2H, m) | 197.2–200.2 |
| 65 | phenyl | 8-Br | 1678, 1453, 1302, 1216, 1121 | 3.12(2H, t), 4.78(2H, t), 7.52–7.61(3H, m), 7.75(1H, d), 7.85–7.96 (2H, m), 8.04(1H, d) | 214.3–215.0 |
| 66 | phenyl | 8-I | 1677, 1477, 1444, 1299, 1269 | 3.13(2H, t), * 4.77(2H, t), 7.52–7.66 (3H, m), 7.83–7.93 (2H, m), 7.92(1H, d), 8.24(1H, d) | 210.2–212.1 |
| 67 | phenyl | 8-CF₃ | 1690, 1340, 1160, 1110 | 3.17(2H, t), 4.85(2H, t), 7.54–7.66(3H, m), 7.79 (1H, d), 7.95–8.07 (2H, m), 8.34(1H, d) | 155.0–156.3 |

TABLE 8-continued

| Exp. No. | R¹ | R | IR(KBr, cm⁻¹) | NMR(DMSO-d₆, ppm) | M.P. (°C.) |
|---|---|---|---|---|---|
| 68 | phenyl | 9-CH₃ | 1690, 1680, 1605, 1440, 1345 | 2.64(3H, s), 3.04(2H, t), 4.73(2H, t), 7.14(1H, d), 7.45–7.62(4H, m), 7.86–8.02(2H, m) | 114.5–115.8 |
| 69 | —CH₂—phenyl | 9-Cl | 3060, 1693, 1595, 1293, 1126 | 3.00(2H, t), 4.37(2H, s), 4.50(2H, t), 7.23–7.50 (6H, m), 7.60(1H, d) | 188.6–190.1 |
| 70 | phenyl-O-ethyl | 9-Cl | 1694, 1598, 1239, 1229, 1126 | 3.06(2H, t), 4.69(2H, t), 5.49(2H, s), 6.82–7.54 (5H, m), 7.39(1H, d), 7.58(1H, d) | oil |
| 71 | —CH₂-thienyl | 9-Cl | 1695, 1685, 1654, 1594, 1128 | 2.97(2H, t), *, 4.33(2H, t), 4.56(2H, s), 6.93(2H, d), 7.16–7.24 (1H, m), 7.28(1H, d), 7.58(1H, d) | 136.1–136.7 |
| 72 | -n-C₈H₁₇- | 9-Cl | 2918, 1697, 1597, 1122 | 0.71–0.99(3H, m), 1.13–1.54(10H, m), 1.59–1.97 (2H, m), 2.92(2H, t), 3.03(2H, t), 4.55(2H, t), 7.29(1H, d), 7.48(1H, d) | 95.2–96.0 |
| 73 | propyl-phenyl | 9-Cl | 1698, 1678, 1598, 1125 | 2.96(2H, t), 3.12–3.19 (4H, m), 4.44(2H, t), 7.20–7.36(6H, m), 7.49 (1H, d) | 117.0–121.0 |
| 74 | propyl-cyclohexyl | 9-Cl | 2935, 2923, 1692, 1596, 1124 | 1.06–1.40(6H, m), 1.45–1.80(7H, m), 2.83–3.02(2H, m), 3.03(2H, t), 4.54(2H, t), 7.29(1H, d), 7.48(1H, d) | 125.1–128.6 |
| 75 | —CH₂CH₂OH | 9-Cl | 3385, 1684, 1661, 1577, 1397 | 2.51–2.69(2H, m), 2.70 (2H, t), 3.72(2H, t), 4.09(2H, t), 5.38–5.49 (1H, b), 7.32(2H, s) | 172.5–174.2 |
| 76 | butyl-phenyl | 9-Cl | 1639, 1596, 1341, 1125, 1087 | 21.5(2H, dt), 2.76 (2H, t), 2.86(2H, t), 3.02(2H, t), 4.51(2H, t), 7.18–7.37(6H, m), 7.49 (1H; d) | 129.5–131.0 |
| 77 | —CH(CH₃)₂ | 9-Cl | 2974, 1694, 1598, 1289 | 1.37(6H, d), 3.05(2H, t), 3.19–3.50(1H, m), 4.59 (2H, t), 7.31(1H, d), 7.50(1H, d) | 128.2–128.8 |
| 78 | —C(CH₃)₃ | 9-Cl | 2980, 1685, 1598, 1129 | 1.50(9H, s), 3.04(2H, t), 4.75(2H, t), 7.31(1H, d), 7.51(1H, d) | 157.9–158.8 |
| 79 | —CH(CH₂CH₃)(CH₂CH₃) (isobutyl-like, CH with two CH₃ branches) | 9-Cl | 2964, 1695, 1596, 1127 | 0.84(6H, t), 1.59–2.01 (4H, m), 2.74–2.96 (1H, m), 3.05(2H, t), 4.59(2H, t), 7.32(1H, d), 7.50(1H, d) | oil |

TABLE 8-continued

| Exp. No. | R¹ | R | IR(KBr, cm⁻¹) | NMR(DMSO-d₆, ppm) | M.P. (°C.) |
|---|---|---|---|---|---|
| 80 | CH₃—C(=)—CH₂CH₃ (2-methyl-1-butenyl) | 9-Cl | 2970, 1694, 1594, 1127 | 1.04(3H, t), 1.92(3H, d), 2.66(2H, q), 3.04(2H, t), 4.62(2H, t), 6.20(1H, q), 7.33(1H, d), 7.51(1H, d) | oil |
| 81 | —CH=CH—C₆H₅ | 9-Cl | 1693, 1683, 1596, 1128 | 3.10(2H, t), 4.80(2H, t), 7.22–7.61(6H, m), 7.71–7.89(3H, m) | 253.3 (dec.) |
| 82 | cyclopropyl | 9-Cl | 1691, 1598, 1515, 1365, 1297, 1100 | 1.06–1.29(4H, m), 2.11–2.43(1H, m), 3.06(2H, t), 4.66(2H, t), 7.26(1H, d), 7.44(1H, d) | 187.6–190.6 |
| 83 | cyclohexyl | 9-Cl | 2930, 2851, 1698, 1593, 1126 | 1.20–2.25(10H, m), * 2.75–3.05(1H, m), 3.07(2H, t), 4.51(2H, t), 7.27(1H, d), 7.60(1H, d) | 136.0–139.0 |
| 84 | cyclohex-3-enyl | 9-Cl | 2940, 1685, 1596, 1260, 1127 | 1.54–2.44(5H, m), 2.91–3.21(1H, m), 3.04(2H, t), 4.61(2H, t), 5.79(2H, m), 7.32(1H, d), 7.51(1H, d) | oil |
| 85 | cyclohex-1-enyl | 9-Cl | 1695, 1683, 1596, 1456, 1130 | 1.58–1.93(4H, m), 2.30–2.60(4H, m), 3.04(2H, t), 4.68(2H, t), 6.50–6.60 (1H, m), 7.34(1H, d), 7.51(1H, d) | 167.9–169.2 |
| 86 | 2-chlorocyclohex-1-enyl | 9-Cl | 1697, 1595, 1340, 1306, 1129 | 1.69–1.91(4H, m), 2.20–2.79(4H, m), 3.04(2H, t), 4.51(2H, t), 7.38(1H, d), 7.57(1H, d) | 193.8–196.0 |
| 87 | 4-F-C₆H₄ | 9-Cl | 1692, 1600, 1234, 1158, 1131 | 3.08(2H, t), 4.78(2H, t), 7.31–7.62(4H, m), 8.05(2H, dd) | 212.1–221.4 |
| 88 | 4-Cl-C₆H₄ | 9-Cl | 1692, 1597, 1460, 1406, 1130 | 3.12(2H, t), * 4.71(2H, t), 7.37(1H, d), 7.53(2H, d), 7.69(1H, d), 7.85(2H, d) | 193.8–195.0 |
| 89 | 2-CH₃-C₆H₄ | 9-Cl | 1685, 1593, 1342, 1130 | 2.40(3H, s), * 3.06(2H, t), 4.38(2H, t), 7.25–7.47(5H, m), 7.69(1H, d) | 135.0–137.5 |
| 90 | 4-OCH₃-C₆H₄ | 9-Cl | 1698, 1687, 1615, 1464, 1261 | 3.08(2H, t), 3.87(3H, s), 4.78(2H, t), 7.15(2H, d), 7.37(1H, d), 7.55(1H, d), 7.95(2H, d) | 168.1–172.6 |

TABLE 8-continued

| Exp. No. | R¹ | R | IR(KBr, cm⁻¹) | NMR(DMSO-d₆, ppm) | M.P. (°C.) |
|---|---|---|---|---|---|
| 91 | 4-N(C₂H₅)₂-phenyl | 9-Cl | 2967, 1683, 1608, 1463, 1342 | 1.15(6H, t), 3.08(2H, t), 3.21–3.67(4H, m), 4.78(2H, t), 6.84(2H, d), 7.34(1H, d), 7.51(1H, d), 7.83(2H, d) | 135.0–138.4 |
| 92 | 2,4-dichlorophenyl | 9-Cl | 1690, 1602, 1591, 1344, 1127 | 3.08(2H, t), 4.46*(2H, t), 7.41(1H, d), 7.43(1H, dd), 7.58(1H, d), 7.64(1H, d), 7.72(1H, d) | 185.0–190.0 |
| 93 | 2-naphthyl | 9-Cl | 1693, 1594, 1128, 748 | 3.15(2H, t), 4.94(2H, t), 7.44(1H, d), 7.56–7.72(3H, m), 7.99–8.22(4H, m), 8.61(1H, s) | 192.2–195.5 |
| 94 | 1-naphthyl | 9-Cl | 1687, 1601, 1592, 1347, 1130 | 3.07(2H, t), 4.47(2H, t), 7.47(1H, d), 7.57–7.95(5H, m), 8.04–8.28(3H, m) | 202.4–207.1 |
| 95 | 4-methoxy-1-naphthyl | 9-Cl | 1685, 1591, 1582, 1274, 1096 | 3.07(2H, t), 4.09(3H, s), 4.47(2H, t), 7.18(1H, d), 7.46(1H, d), 7.63(1H, d), 7.56–7.68(2H, m), 7.86(1H, d), 8.11–8.37(2H, m) | 227.4–228.4 |
| 96 | 3-furyl | 9-Cl | 1690, 1585, 1305, 1165, 1120 | 3.12(2H, t), 4.79(2H, t), 7.13(1H, s), 7.40(1H, d), 7.55(1H, d), 7.76(1H, s), 8.44(1H, s) | 259.6–261.0 |
| 97 | 2-furyl | 9-Cl | 2360, 1693, 1589, 1507, 1128 | 3.10(2H, t), 4.92(2H, t), 6.47–6.79(1H, m), 7.35(1H, d), 7.39(1H, d), 7.55(1H, d), 7.99(1H, d) | 272.0–273.09 |
| 98 | 3-thienyl | 9-Cl | 1690, 1595, 1335, 1300, 1120 | 3.11(2H, t), 4.86(2H, t), 7.35(1H, d), 7.55(1H, d), 7.76(1H, d), 7.77(1H, d), 8.32(1H, dd) | 245.0–246.2 |
| 99 | 5-bromo-2-thienyl | 9-Cl | 1694, 1598, 1466, 1130, | 3.12(2H, t), 4.87(2H, t), 7.40(1H, d), 7.44(1H, d), 7.57(1H, d), 7.74(1H, d) | 245.3–247.5 |
| 100 | 3-pyridyl | 9-Cl | 1695, 1595, 1340, 1195 | 3.11(2H, t), 4.83(2H, t), 7.44(1H, d), 7.62(1H, d), 7.47–7.70(1H, m), 8.10–8.47(1H, m), 8.79(1H, dd), 9.17(1H, dd) | 191.7–193.4 |

TABLE 8-continued

Structure: quinolinone with N=CH-R¹ at position 8, R at position 6, ketone at position 4

| Exp. No. | R¹ | R | IR(KBr, cm⁻¹) | NMR(DMSO-d₆, ppm) | M.P. (°C.) |
|---|---|---|---|---|---|
| 101 | tetrahydropyran-4-yl | 9-Cl | 2949, 2850, 1694, 1593, 1128 | 1.66–2.19(4H, m), 3.04 (2H, t), 3.19–3.49 (1H, m), 3.34–3.76 (2H, m), 3.89–4.23 (2H, m), 4.61(2H, t), 7.31(1H, d), 7.50(1H, d) | 148.3–149.6 |
| 102 | quinolin-4-yl | 9-Cl | 1685, 1675, 1600, 1586, 1305, 1131 | 3.08(2H, t), 4.58(2H, t), 7.50(1H, d), 7.68(1H, d), 7.63–8.00(2H, m), 7.89(1H, d), 8.10–8.44 (2H, m), 9.12(1H, d) | 207.3–216.8 |
| 103 | 5-methoxy-3-methylindol-2-yl | 9-Cl | 1689, 1601, 1562, 1243, 1233 | 3.12(2H, t), 3.84(3H, s), 4.85(2H, t), 6.92 (1H, dd), 7.17–7.46 (3H, m), 8.06(1H, d), 8.20(1H, d), 11.50–12.30(1H, b) | 292.6–295.3 |

NMR data marked with asterisks (*) were measured in CDCl₃.

TABLE 9

Structure: 8-amino-4-oxo-tetrahydroquinoline with R substituent

| Exp. No. | R | IR(KBr, cm⁻¹) | NMR(DMSO-d₆, ppm) | M.P. (°C.) |
|---|---|---|---|---|
| 104 | 5-Cl | 3373, 1658, 1654, 1600, 1500, 1269 | 2.52(2H, t), 3.47(2H, t), 4.82(2H, bs), 6.05(1H, b), 6.40(1H, d), 6.60(1H, d)) | 153.1–154.5 |
| 105 | 6-F | 3268, 1656, 1618, 1510, 1311, 1152 | 2.50(2H, t), 3.45(2H, t), 5.17(2H, bs), 5.77(1H, b), 6.34–6.69(2H, m) | 110.0–112.0 |
| 106 | 6-Br | 3364, 1654, 1507, 1338, 1155 | 2.52(2H, t), 3.47(2H, t), 5.09(2H, bs), 6.06(1H, b), 6.75(1H, d), 7.01(1H, d) | 151.2–152.3 |
| 107 | 6-I | 3376, 1664, 1654, 1636, 1595, 1508 | 2.49(2H, t), 3.46(2H, t), 4.94(2H, bs), 6.05(1H, b), 6.90(1H, d), 7.20(1H, d) | 134.7–136.7 |
| 108 | 6-CF₃ | 3397, 1652, 1620, 1337, 1097 | 2.56(2H, t), 3.55(2H, t), 4.54(2H, bs), 6.51(1H, b), 6.86(1H, d), 7.28(1H, d) | 152.0–153.1 |
| 109 | 7-CH₃ | 3365, 1654, 1601, 1506, 1246 | 2.07(3H, s), 2.46(2H, t), 3.46(2H, t), 4.54(2H, bs), 5.87(1H, b), 6.37(1H, d), 6.97(1H, d) | 104.6–106.0 |

TABLE 10

Structure: 8-nitro-4-oxo-tetrahydroquinoline with R substituent

| Exp. No. | R | IR(KBr, cm⁻¹) | NMR(DMSO-d₆, ppm) | M.P. (°C.) |
|---|---|---|---|---|
| 110 | 5-Cl | 1695, 1602, 1567, 1264, 1075 | 2.70(2H, t), 3.72(2H, dt), 6.71(1H, d), 8.20(1H, d), 8.94(1H, b) | 171.6–173.0 |
| 111 | 6-F | 3388, 1691, 1514, 1264, 1172 | 2.71(2H, t), 3.69(2H, dt), 7.85(1H, dd), 8.17(1H, dd), 8.54(1H, b) | 154.3–156.2 |
| 112 | 6-Br | 3392, 1694, 1615, 1508, 1405, 1259 | 2.69(2H, t), 3.68(2H, dt), 7.98(1H, d), 8.34(2H, d), 8.67(1H, b) | 153.7–155.3 |
| 113 | 6-I | 3353, 1492, 1341, 1263, 1152 | 2.71(2H, t), 3.61(2H, t), 8.21(1H, d), 8.29(1H, d), 10.4(1H, b) | 238.2–242.5 |
| 114 | 6-CF₃ | 3396, 1699, 1634, 1319, 1258, 1117 | 2.75(2H, t), 3.77(2H, dt), 8.12(1H, d), 8.47(1H, d), 8.97(1H, b) | 120.6–123.2 |
| 115 | 7-CH₃ | 3352, 1670, 1609, 1530, 1506, 1268 | 2.33(3H, s), 2.51(2H, t), 3.54(2H, dt), 6.61(1H, d), 7.26(1H, b), 7.74(1H, d) | 167.9–170.1 |

Now, typical but non-limiting examples of formulations of the compound of this invention will be shown below.

FORMULATION A (CAPSULES)

Compound 1, 50 g of weight, 935 g of lactose and 15 g of magnesium stearate were weighed and mixed until the mixture became homogeneous. The mixture was then filled in No. 1 hard gelatin capsule at 200 mg each to obtain capsule preparations.

FORMULATION B (TABLETS)

Compound 3, 50 g of weight, 755 g of lactose, 165 g of potato starch, 15 g of polyvinyl alcohol and 15 g of magnesium stearate were weighed. The weighed amount of compound 3, lactose and potato starch were mixed until accomplishing homogeneity. Then aqueous solution of polyvinylalcohol was added to the mixture, then the resulting mixture was granulated by wet process. The granules were then dried, mixed with magnesium stearate and pressed into tablets, each weighing 200 mg.

FORMULATION C (POWDERS)

Compound 2, 2 g of weight, 97 g of lactose and 1 g of magnesium stearate were weighed and mixed until the mixture became homogeneous to obtain 2% powder preparations.

FORMULATION D (RECTAL SUPPOSITORIES)

Compound 5, 10 g of weight, 200 g of polyethyleneglycol 1500 and 790 g of polyethyleneglycol 4000 were ground well in a mortar and formulated into suppository by melting and casting into 1 g of appropriate mold.

FORMULATION E (INJECTIONS)

Compound 8, 0.1 g of weight, 0.9 g of sodium chloride and suitable amount of sodium hydroxide were dissolved in 100 ml of distilled water for injection. The solution was filtered and sterilized. 5 ml each of the sterilized solution was poured into 10-ml ampoules and sealed to obtain preparations for injection.

FORMULATION F (EYE DROPS)

Compound 6, 0.5 g of weight, 12 g of glycerin, 5 g of sodium chloride and suitable amount of sodium hydroxide was dissolved in 1000 ml of distilled water. The solution was filtered, sterilized. The sterilized solution was divided into vials to obtain preparation for eye drops.

FORMULATION G (LIPOSOMES)

To a solution of yolk phosphatidyl choline (2 mmol) in diethyl ether (120 ml) was added cholesterol (2 mmol) and vitamin E (20 μmol), then mixed. To the mixture was added 2 mM solution of compound 18 (20 ml). The resulting mixture was stirred by voltexmixer for 1 minute, then treated with supersonic waves for 15 seconds under cooling at 2° C. After removing the solvent by distillation, formed liposome (20 ml) was divided into 10 ml-ampoules by 5 ml of each.

What is claimed is:

1. A 4,5-dihydro-6H-imidazo[4,5,1-ij]quinolin-6-one-6-oxime-O-sulfonic acid compound represented by the formula (I):

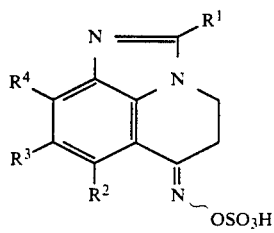

wherein $R^1$ represents $-(A)_m B$ wherein A represents an alkylene of straight or branched chain having 1 to 10 carbon atoms, an alkenylene of straight or branched chain having 2 to 10 carbon atoms, B represents a hydrogen atom, a hydroxy group, a cycloalkyl or cycloalkenyl group having 3 to 8 carbon atoms, a phenyl group, a phenoxy group, a naphthyl group or a mono- or fused- heterocyclic group selected from the group consisting of furyl, tetrahydropyranyl, quinolinyl, indolyl, pyridyl, and thienyl; any one of which is unsubstituted or substituted with one or more substituents which are identical or different and selected from a group consisting of a halogen atom, an alkyl group having 1 to 4 carbon atoms, an alkoxy group having 1 to 4 carbon atoms, a nitro group and an alkylamino group having 1 to 4 carbon atoms, m represents 0 or an integer of 1 and $R^2$, $R^3$ and $R^4$ are identical or different and represent hydrogen atoms, halogen atoms, hydroxy groups, alkyl groups having 1 to 4 carbon atoms, alkoxy groups having 1 to 4 carbon atoms, or halogenated alkyl groups having 1 to 4 carbon atoms, provided that at least one of $R^2$, $R^3$ and $R^4$ represents a hydrogen atom, and that two adjacent groups of $R^2$, $R^3$ and $R^4$ are not groups at the same time selected from a group consisting of branched alkyl groups, branched alkoxy groups and branched halogenated alkyl groups, and the bond shown with a wavy line represents a bond of E-form or Z-form, or a salt or a solvate or a solvate of said salt thereof.

2. A 4,5-dihydro-6H-imidazo[4,5,1-ij]quinolin-6-one-6-oxime-O-sufonic acid compound as claimed in claim 1 wherein m represents 0.

3. A 4,5-dihydro-6H-imidazo[4,5,1-ij]quinolin-6-one-6-oxime-O-sulfonic acid compound as claimed in claim 2 wherein B represents a cycloalkyl or cycloalkenyl group, optionally substituted with one or more halogen atoms.

4. A 4,5-dihydro-6H-imidazo[4,5,1-ij]quinolin-6-one-6-oxime-O-sulfonic acid compound as claimed in claim 2 wherein B represents a phenyl group which may be substituted with one or more substituents selected from a group consisting of a halogen atom, an alkyl group having 1 to 4 carbon atoms, an alkoxy group having 1 to 4 carbon atoms, a nitro group or a N,N-diethylamino group.

5. A 4,5-dihydro-6H-imidazo[4,5,1-ij]quinolin-6-one-6-oxime-O-sulfonic acid compound as claimed in claim 2 wherein B represents a phenoxy group.

6. A 4,5-dihydro-6H-imidazo[4,5,1-ij]quinolin-6-one-6-oxime-O-sulfonic acid compound as claimed in claim 2 wherein B represents a naphthyl group optionally substituted with one or more alkoxy groups having 1 to 4 carbon atoms.

7. A 4,5-dihydro-6H-imidazo[4,5,1-ij]quinolin-6-one-6-oxime-O-sulfonic acid compound as claimed in claim 2 wherein B represents a mono- or fused-heterocyclic group optionally substituted with one or more halogen atoms or alkoxy groups having 1 to 4 carbon atoms.

8. A 4,5-dihydro-6H-imidazo[4,5,1-ij]quinolin-6-one-6-oxime-O-sulfonic acid compound as claimed in claim 1 wherein m represents an integer of 1.

9. A 4,5-dihydro-6H-imidazo[4,5,1-ij]quinolin-6-one-6-oxime-O-sulfonic acid compound as claimed in claim 8 wherein B represents a cycloalkyl or cycloalkenyl group, optionally substituted with one or more halogen atoms.

10. A 4,5-dihydro-6H-imidazo[4,5,1-ij]quinolin-6-one-6-oxime-O-sulfonic acid compound as claimed in claim 8 wherein B represents a phenyl group optionally substituted with one or more substituents selected from a group consisting of a halogen atom, an alkyl group having 1 to 4 carbon atoms, an alkoxy group having 1 to 4 carbon atoms, a nitro group or a N,N-diethylamino group.

11. A 4,5-dihydro-6H-imidazo[4,5,1-ij]quinolin-6-one-6-oxime-O-sulfonic acid compound as claimed in claim 8 wherein B represents a phenoxy group.

12. A 4,5-dihydro-6H-imidazo[4,5,1-ij]quinolin-6-one-6-oxime-O-sulfonic acid compound as claimed in claim 8 wherein B represents a mono- or fused-heterocyclic group optionally substituted with one or more halogen atoms or alkoxy groups having 1 to 4 carbon atoms.

13. A 4,5-dihydro-6H-imidazo[4,5,1-ij]quinolin-6-one-6-oxime-O-sulfonic acid compound as claimed in claim 1 wherein at least one of $R^2$, $R^3$ or $R^4$ represents a halogen atom.

14. A 4,5-dihydro-6H-imidazo[4,5,1-ij]quinolin-6-one-6-oxime-O-sulfonic acid compound as claimed in claim 13 wherein $R^4$ represents a halogen atom, and $R^2$ and $R^3$ represent hydrogen atoms.

15. A 4,5-dihydro-6H-imidazo[4,5,1-ij]quinolin-6-one-6oxime-O-sulfonic acid compound as claimed in claim 1 wherein the bond shown with a wavy line represents a bond of E-form.

16. A pharmaceutical composition which comprises a pharmaceutically acceptable carrier and an effective amount of at least one of a 4,5-dihydro-6H-imidazo[4,5,1-ij]quinolin-6-one-6-oxime-O-sulfonic acid compound represented by the formula (I):

wherein $R^1$ represents $$+A+_m B$$

wherein A represents an alkylene of straight or branched chain having 1 to 10 carbon atoms, an alkenylene of straight or branched chain having 2 to 10 carbon atoms, B represents a hydrogen atom, a hydroxy group, a cycloalkyl or cycloalkenyl group having 3 to 8 carbon atoms, a phenyl group, a phenoxy group, a naphthyl group or a mono- or fused- heterocyclic group selected from the group consisting of furyl, tetrahydropyranyl, quinolinyl, indolyl, pyridyl, and thienyl; any one of which is unsubstituted or substituted with one or more substituents which are identical or different and selected from a group consisting of a halogen atom, an alkyl group having 1 to 4 carbon atoms, an alkoxy group having 1 to 4 carbon atoms, a nitro group and an alkylamino group having 1 to 4 carbon atoms, m represents 0 or an integer of 1 and $R^2$, $R^3$ and $R^4$ are identical or different and represent hydrogen atoms, halogen atoms, hydroxy groups, alkyl groups having 1 to 4 carbon atoms, alkoxy groups having 1 to 4 carbon atoms, or halogenated alkyl groups having 1 to 4 carbon atoms, provided that at least one of $R^2$, $R^3$ and $R^4$ represents a hydrogen atom, and that two adjacent groups of $R^2$, $R^3$ and $R^4$ are not groups at the same time selected from a group consisting of branched alkyl groups, branched alkoxy groups and branched halogenated alkyl groups, and the bond shown with a wavy line represents a bond of E-form or Z-form, or a salt or a solvate or a solvate of said salt thereof.

17. A pharmaceutical composition as claimed in claim 16 wherein m represents 0.

18. A pharmaceutical composition as claimed in claim 17 wherein B represents a cycloalkyl or cycloalkenyl group, optionally substituted with one or more halogen atoms.

19. A pharmaceutical composition as claimed in claim 17 wherein B represents a phenyl group which may be substituted with one or more substituents selected from a group consisting of a halogen atom, an alkyl group having 1 to 4 carbon atoms, an alkoxy group having 1 to 4 carbon atoms, a nitro group or a N,N-diethylamino group.

20. A pharmaceutical composition as claimed in claim 19 wherein B represents a phenoxy group.

21. A pharmaceutical composition as claimed in claim 17 wherein B represents a naphthyl group optionally substituted with one or more alkoxy groups having 1 to 4 carbon atoms.

22. A pharmaceutical composition as claimed in claim 17 wherein B represents a mono- or fused-heterocyclic group optionally substituted with one or more halogen atoms or alkoxy groups having 1 to 4 carbon atoms.

23. A pharmaceutical composition as claimed in claim 16 wherein m represents an integer of 1.

24. A pharmaceutical composition as claimed in claim 23 wherein B represents a cycloalkyl group or a cycloalkenyl group, optionally substituted with halogen atoms.

25. A pharmaceutical composition as claimed in claim 23 wherein B represents a phenyl group which may be substituted with one or more substituents selected from a group consisting of a halogen atom, an alkyl group having 1 to 4 carbon atoms, an alkoxy groups having 1 to 4 carbon atoms, a nitro group or a N,N-diethylamino group.

26. A pharmaceutical composition as claimed in claim 23 wherein B represents a phenoxy group.

27. A pharmaceutical composition as claimed in claim 23 wherein B represents a mono- or fused-heterocyclic group optionally substituted with one or more halogen atoms or alkoxy groups having 1 to 4 carbon atoms.

28. A pharmaceutical composition as claimed in claim 2 wherein at least one of $R^2$, $R^3$ or $R^4$ represents a halogen atom.

29. A pharmaceutical composition as claimed in claim 28 wherein $R^4$ represents a halogen atom, and $R^2$ and $R^3$ represent hydrogen atoms.

30. A pharmaceutical composition as claimed in claim 2 wherein the bond shown with a wavy line represents a bond of E-form.

* * * * *